(12) United States Patent
Flugelman

(10) Patent No.: US 7,943,590 B2
(45) Date of Patent: May 17, 2011

(54) COMPOSITIONS AND METHODS FOR TREATING OPHTHALMIC DISORDERS

(75) Inventor: Moshe Flugelman, Haifa (IL)

(73) Assignee: Multi-Gene Vascular Systems Ltd., Haifa (IL)

( * ) Notice: Subject to any disclaimer, the term of this patent is extended or adjusted under 35 U.S.C. 154(b) by 234 days.

(21) Appl. No.: 12/075,992

(22) Filed: Mar. 14, 2008

(65) Prior Publication Data

US 2008/0227692 A1    Sep. 18, 2008

Related U.S. Application Data

(60) Provisional application No. 60/918,539, filed on Mar. 16, 2007.

(51) Int. Cl.
*A01N 43/04*     (2006.01)
*A01N 63/00*     (2006.01)
*A61K 31/715*    (2006.01)
*A61K 48/00*     (2006.01)

(52) U.S. Cl. .................. 514/44; 424/93.2; 424/93.21

(58) Field of Classification Search .............. 424/93.21, 424/93.2; 514/44
See application file for complete search history.

(56) References Cited

FOREIGN PATENT DOCUMENTS

WO    WO 00/41712    7/2000

OTHER PUBLICATIONS

Iwaguro (Circulation, 2002, vol. 105, p. 732-738).*
Chen et al., "Combination of $VEGF_{165}$/Angiopoietin-1 gene and endothelial progenitor cells for therapeutic neovascularization" *Eur. J. Pharmacol.*, 568:222-230 92007).
Gluzman et al., "Endothelial cells are activated by angiopoeitin-1 gene transfer and produce coordinated sprouting in vitro and arteriogenesis in vivo", *Biochem. Biophys, Res. Comm.*, 359:263-268 (2007).
Joussen et al., "Suppression of Diabetic Retinopathy with Angiopoietin-1", *Am. J. Pathol.*, 160(5):1683-1693 (2002).
Nambu et al., "Angiopoietin 1 Prevents Retinal Detachment in an Aggressive Model of Proliferative Retinopathy, but has no Effect on Established Neovascularization", *J. Cell. Physiol.*, 204:227-235 (2005).

* cited by examiner

*Primary Examiner* — Michael C. Wilson
(74) *Attorney, Agent, or Firm* — Mintz Levin Cohn Ferris Glovsky and Popeo, P.C.; Ivor R. Elrifi; Matthew Pavao

(57) ABSTRACT

The present invention relates to compositions and methods for treating and/or preventing ocular disorders, diseases or conditions and compositions and methods for treating or preventing ophthalmic conditions and disorders in a subject in need thereof.

4 Claims, 16 Drawing Sheets

COMPOSITIONS AND METHODS FOR TREATING OPHTHALMIC DISORDERS

RELATED U.S. APPLICATIONS

This application claims priority to U.S. Ser. No. 60/918,539 filed Mar. 16, 2007, which is incorporated herein by reference in its entirety.

FIELD OF THE INVENTION

The present invention relates to compositions and methods for treating and/or preventing ocular disorders, diseases or conditions and compositions and methods for treating or preventing ophthalmic conditions and disorders in a subject in need thereof.

BACKGROUND

Diabetic retinopathy (DR) remains the most common cause of vision impairment in working-age adults in the United States and Europe, and retinal neovascularization occurs in up to 20% of patients with diabetes. The current treatment of ablating the peripheral retina, while effective in reducing the risk of severe vision loss, is only applied after the onset of neovascularization, does not address the basic biological abnormality that leads to this complication, reduces peripheral and night vision, and is uncomfortable and expensive. So far, there is no clinically proven non-surgical alternative. Anti-VEGF therapies, which are already used to treat ocular neovascularization in age-related macular degeneration (AMD), raise concerns for diabetic patients; antagonism of VEGF might interfere with myocardial revascularization in patients who are already at high risk for cardiac ischemia, for example, and loss of the neurotrophic and vasculotrophic actions of VEGF might exacerbate neuronal loss and ischemia in diabetic eyes. Therapies that address the multifactorial nature of retinopathy will probably be more successful than single-molecule-specific approaches (Gariano & Gardner, *Nature* 438, 960-966, 2005).

Pathological retinal neovascularization in patients with diabetes results from an imbalance of pro-angiogenic and anti-angiogenic factors. In addition to VEGF accumulation in eyes with diabetic retinal neovascularization, changes in numerous other cytokines, chemokines, adhesion molecules, vasoactive hormones and immune cells have been reported. Together, these changes constitute a complex inflammatory process that results in an aberrant wound-healing response. Recent work shows that all retinal cell types, including neurons, glial, microglial and vascular cells, are affected by diabetes, resulting in a neurovascular disorder. The retinal neurovascular degeneration of diabetes includes neuronal and vascular cell apoptosis, and microglial and glial cell activation, which provides intraretinal sources of cytokines and chemokines (Gariano & Gardner, *Nature* 438, 960-966, 2005).

Clinically, diabetic retinopathy (DR) is classified into two stages: non-proliferative DR (NPDR) and proliferative DR (PDR). In NPDR, VEGF-A (which is known to act as a survival factor for endothelial cells, via induction of anti-apoptotic proteins) expression in elevated levels has been described in human and in experimental models of DR. VEGFRs are also upregulated in NPDR. VEGF-A may be increased initially in preclinical DR as a mechanism to maintain the integrity of the retinal vascular bed. In a later stage, high VEGF-A production in ischemic areas, where VEGFR-2 is upregulated, then leads to vascular leakage and neovascularisation. In proliferative DR (PDR), intra-ocular neovascularisation is likely caused by high levels of VEGF-A in the vitreous derived from widespread production of this factor by ischemic retina. Elevated levels of VEGF-A have been found in the aqueous humor and vitreous of patients with PDR (Witmer et al., *Prog Ret Eye Res* 22, 1-29, 2003).

Age-Related Macular Degeneration (AMD) is one of the leading causes of irreversible vision loss in the Western world, accounting for 75% of legal blindness in the population of age 50 years old or older in the developed countries (Zhang & Ma, *Prog Ret Eye Res* 26, 1-37, 2007).

Two subgroups of AMD are classically distinguished: atrophic (dry form) and exudative (wet form). The dry form (also known as geographic atrophy, both central and/or non-central) is typically characterized by a progressing course leading to degeneration of retinal pigment epithelium (RPE) and photoreceptors. The exudative form is linked to choroidal neovascularization (CNV, the abnormal growth of blood vessels that originate from the choroidal vasculature) directed to the subretinal macular region, with subsequent bleeding and/or fluid leakage, which may result in a sudden loss of central vision; it is the most rapidly progressing form of AMD. Clinical features common for the two types of AMD include the presence of drusen, which is defined as the complex deposits of lipids, proteins, and inflammatory mediators that develop in the Bruch's membrane under the RPE, as well as hypo- and/or hyperpigmentation of the RPE. More than 80% of all people with intermediate and advanced AMD have the dry form, yet this form may progress to the wet form which leads to significantly more vision loss (Zhang & Ma, *Prog Ret Eye Res* 26, 1-37, 2007; Nowak, *Pharmacol Reports* 58, 353-363, 2006).

The pathophysiology of AMD is complex and, in addition to genetic predispositions, at least four processes contribute to the disease, i.e. lipofuscinogenesis (with its linkage to oxidative stress), drusogenesis, local inflammation and neovascularization (in the case of wet form). In order to stimulate the process of angiogenesis, including CNV, the angiogenesis-linked molecular machinery must be disbalanced in a way promoting functional overactivity of pro-angiogenic signaling. This may result from either an unbalanced increase in pro-angiogenic (e.g. VEGF) activity or an unbalanced decrease in anti-angiogenic (e.g. pigment epithelium derived factor, PEDF) activity. Despite many similarities in the pathways leading to the retinal and choroidal neovascularization, there are some major differences between these two types of angiogenesis. Current view suggests that in the initiation and development of CNV, there may be a role for local inflammation together with immune reactions as a process creating cellular and molecular milieu promoting the prevalence of pro-angiogenic mechanisms; in fact, neutrophils, macrophages, mast cells, activated microglia, all are capable of producing and releasing an array of pro-angiogenic factors, including VEGF. Recent findings confirm the role of VEGF and PEDF as important regulators engaged in CNV, and this fact has already its impact on establishing therapeutic strategies to combat the existing or to prevent the development of newly formed unwanted blood vessels (Nowak, *Pharmacol Reports* 58, 353-363, 2006).

In patients with AMD, high levels of VEGF and VEGF receptor have been detected in the subfoveal fibrovascular membrane, the surrounding tissues and the RPE (Zhang & Ma, *Prog Ret Eye Res* 26, 1-37, 2007).

Thus, there remains a need for safe, effective, non-invasive and inexpensive compositions and methods to treat and/or prevent various ophthalmic and ocular disorders, such as DR and AMD. The present invention provides such methods and compositions.

SUMMARY OF THE INVENTION

The present invention relates to compositions and methods for treating and/or preventing ophthalmic or ocular disorders, diseases or conditions and compositions and methods for treating or preventing ophthalmic or ocular conditions and disorders in a subject in need thereof.

The subject is preferably a mammal in need of such treatment. Suitable mammals include, e.g., any mammal, e.g., a human, a primate, mouse, rat, dog, cat, cow, horse, pig. Preferably, the mammal is a human.

The invention provides ophthalmic compositions for treating an ophthalmic condition or disorder comprising angiopoietin-1 (Ang-1) and/or Fibulin 5 and a pharmaceutically acceptable carrier. In one aspect, the composition further comprises endothelial cells comprising a nucleic acid construct comprising a polynucleotide sequence encoding the Ang-1 operably linked to a promoter such that the endothelial cells express or over-express the Ang-1. Optionally, the endothelial cells are autologous. Alternatively, the endothelial cells are exogenous.

In another aspect, the composition further comprises endothelial cells comprising a nucleic acid construct comprising a polynucleotide sequence encoding the Fibulin 5 operably linked to a promoter such that the endothelial cells express or over-express the Fibulin 5. Optionally, the endothelial cells are autologous. Alternatively, the endothelial cells are exogenous.

In one aspect, the composition is in the form of eye drops, ointment, gel, or an ocular insert.

The invention provides compositions wherein the Fibulin 5 is full-length human Fibulin 5 polynucleotide or full-length human Fibulin 5 polypeptide. The invention also provides compositions wherein the Ang-1 is Ang-1 polynucleotide or Ang-1 polypeptide.

The invention also provides methods of treating an ophthalmic condition or disorder comprising administering a therapeutically effective amount of Ang-1 and/or Fibulin 5 to a subject in need thereof. Suitable ophthalmic disorders include diabetic retinopathy and age-related macular degeneration (AMD).

In one aspect, the method comprises administering autologous endothelial cells comprising a nucleic acid construct comprising a polynucleotide sequence encoding the Ang-1 operably linked to a promoter such that the endothelial cells express or over-express the Ang-1. Preferably, the endothelial cells are administered by intravitreal injection. Alternatively, the endothelial cells are administered intravenously.

In another aspect, the method comprises administering autologous endothelial cells comprising a nucleic acid construct comprising a polynucleotide sequence encoding the Fibulin 5 operably linked to a promoter such that the endothelial cells express or over-express the Fibulin 5. Preferably, the endothelial cells are administered by intravitreal injection. Alternatively, the endothelial cells are administered intravenously.

Preferably, the Ang-1 induces angiogenesis, enhances endothelial cell survival, or prevents vascular leakage.

The invention also provides methods of inducing retinopathy in a mammal comprising administering an effective amount of VEGF. Preferably, the mammal is non-diabetic. In one aspect, the mammal is non-human. In one aspect, the method comprises administering autologous smooth muscle cells comprising a nucleic acid construct comprising a polynucleotide sequence encoding the VEGF operably linked to a promoter such that the smooth muscle cells express or over-express the VEGF. Preferably, the smooth muscle cells are administered by intravitreal injection.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following description of the preferred embodiments thereof, and from the claims.

DETAILED DESCRIPTION

Figure 1:
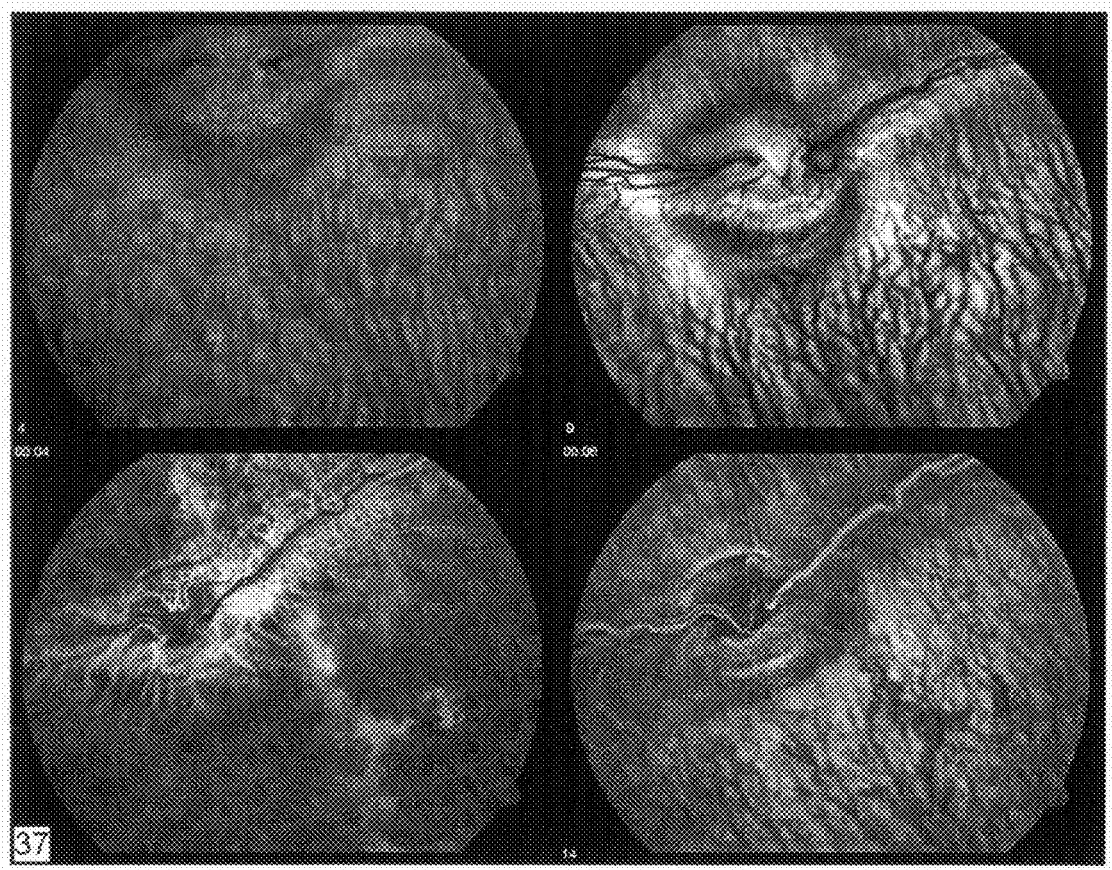
FIG. 1 is a series of photographs showing the normal architecture of the retinal blood vessels in a rabbit.

The present invention provides methods and compositions for treating and/or preventing ophthalmic or ocular disorders, diseases or conditions and compositions and methods for treating or preventing ophthalmic or ocular conditions and disorders in a subject in need thereof. Examples of these conditions include diabetic retinopathy, age-related macular degeneration, cataracts, glaucoma, presbyopia, or dry eye syndrome. Preferably, the present invention is directed to treating and/or preventing diabetic retinopathy and age-related macular degeneration. The terms "ophthalmic" and "ocular" are used interchangeably herein.

Angiopoietin-1 (Ang-1) (GenBank Accession Number NM_001146, BC152419, BC152411, BC029406, AY124380, AY121504, AB084454, U83508, NP_001137, BAB91325, AAB50557, AAM92271, AAI52420, AAI52412, AAM81745, EAW91912, EAW91911, EAW91910, or EAW91909) has potential therapeutic applications in inducing angiogenesis, enhancing endothelial cell survival, and preventing vascular leakage. There are studies that suggest that Ang-1 regulates the maturation of newly formed blood vessels, while other studies suggest that the binding of Ang-2 to it's receptor, Tie2, plays a role in the regression of existing vessels (Suri et al., Cell 87:1171-80, 1996).

The present invention provides methods for treating or preventing at least one ophthalmic disorder in a subject in need thereof by administering a therapeutically effective amount of one or more Ang-1 nucleic acids or peptides or by administering one or more autologous or exogenous endothelial cells that are genetically altered to express or over-express Ang-1 prior to administration.

Fibulin 5 (GenBank Accession Number NM_006329, BC022280, CAB38568, AAH22280, EAW81467, EAW81466, EAW81465, AAD41768, AF112152, AAC62107, or AF093118), which is also known as UP50 or DANCE (Developing Arteries and Neural Crest, EFG-like), is a protein that belongs to a family of extracellular proteins expressed in the basement membranes of blood vessels. It has been implicated in the generation and organization of elastic fibers, which are essential to various organs that require elasticity, such as the lungs, large arteries and skin. This protein has an RGD motif that interacts with cell surface integrins and promote cell to matrix adhesion. Fibulin 5 may be essential for the polymerization of elastin.

The present invention also provides methods for treating or preventing at least one ophthalmic disorder in a subject in need thereof by administering a therapeutically effective amount of one or more fibulin 5 nucleic acids or peptides or by administering one or more autologous or exogenous endothelial cells that are genetically altered to express or over-express fibulin 5 prior to administration.

Additionally, the present invention provides methods treating or preventing at least one ophthalmic disorder by administering both Ang-1 and fibulin 5 to a subject in need thereof.

In an embodiment, one or more Ang-1 and or fibulin 5 nucleic acids or proteins are administered in pharmaceutically acceptable formulations to the subject. In another embodiment, one or more autologous or exogenous endothelial cells are genetically altered to express or over-express Ang-1 or fibulin 5 and those genetically altered cells are administered in pharmaceutically acceptable formulations to the subject.

The subject is preferably a mammal in need of such treatment. The mammal can be e.g., any mammal, e.g., a human, a primate, mouse, rat, dog, cat, cow, horse, pig. In a preferred embodiment, the mammal is a human.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible to a particular adverse condition, disorder, or disease, and thus relates to the prevention of the occurrence of symptoms and/or their underlying cause.

By the terms "effective amount" and "therapeutically effective amount" of a formulation or formulation component is meant a nontoxic but sufficient amount of the formulation or component to provide the desired effect.

The terms "express" and "over-express" are used to denote the fact that, in some cases, a cell useful in the method herein may inherently express some of the factor that it is to be genetically altered to produce, in which case the addition of the polynucleotide sequence results in over-expression of the factor. That is, more factor is expressed by the altered cell than would be, under the same conditions, by a wild type cell. Similarly, if the cell does not inherently express the factor that it is genetically altered to produce, the term used would be to merely "express" the factor since the wild type cell did not express the factor at all.

By "genetically altered" is meant that the genomic content of the cell is altered to include an exogenous nucleic acid sequence not found in the wild type cell, or an additional copy of an endogenous nucleic acid sequence found in the wild type cell, that encodes a vascular proliferation factor or a vascular maturation factor. The alteration can be stable, as in the case, without limitation, of retrovirus infection where the new sequence in integrated into the genome and is passed from generation to generation or it can be transient as in the case, without limitation, of adenovirus infection wherein the new sequence is not passed on.

U.S. Application Publication No. 2004/0151707 describes suitable vectors and methods for genetically altering endothelial cells to express or over express Ang-1. U.S. Pat. No. 7,175,658 describe suitable vectors and methods for genetically altering endothelial cells to express or over express fibulin 5.

In embodiments where Ang-1 and/or Fibulin 5 are expressed or over-expressed in endothelial cells prior to administration, Ang-1 and Fibulin 5 may be expressed from a single promoter sequence in the nucleic acid construct. Various constructs can be used to accomplish this. For example, without limitation, the first and second polynucleotide segments can be transcriptionally fused through a linker sequence that includes an internal ribosome entry site (IRES) sequence. This enables the translation of the polynucleotide segment downstream of the IRES sequence. In this way, a transcribed polycistronic RNA molecule containing the coding sequences of both Ang-1 and Fibulin 5 can be translated from both the capped 5' end and the internal IRES sequence to express the factors.

Alternatively, the first and second polynucleotide segments can be translationally fused through a protease recognition site cleavable by a protease expressed by the cell to be genetically altered. In this case, a single chimeric polypeptide will be expressed and subsequently cleaved by the cell-expressed protease to generate the factors.

The nucleic acid construct can comprise two promoter sequences, which may be the same or different. The promoters are isolated from one another so that the angiogenic proliferating factor and the angiogenic maturation factor are separately transcribed, each from its own dedicated promoter.

Of course, expression of Ang-1 and Fibulin 5 can also be directed by two completely separate nucleic acid constructs inserted into the same cell. The promoters used in the two constructs may be the same or different.

The promoters used in these constructs are preferably constitutive, tissue specific or inducible promoters. Constitutive promoters are those that normally operate in a cell at all times; that is they are not, or at least do not appear to be, subject to quantitative regulation. Inducible promoters, on the other hand, are regulatable and their quantitative operation may be controlled by a specific stimulus. The phrase "tissue specific promoter" is self-explanatory; such promoters only operate in specific tissues.

To generate the nucleic acid constructs, the polynucleotide segment encoding Ang-1 and Fibulin 5 are ligated into commercially available expression vector systems. Such vector systems can easily be modified using recombinant techniques well-known in the art to replace, duplicate or mutate existing promoter or enhancer sequences and/or to introduce additional polynucleotide sequences such as, without limitation, selection markers or reporter polypeptides.

Suitable mammalian expression vectors include, but are not limited to, pcDNA3, pcDNA3.1(+/−), pZeoSV2(+/−), pSecTag2, pDisplay, pEF/myc/cyto, pCMV/myc/cyto and pCR3.1, all of which are available from Invitrogen. They also include pCI, which is available from Promega, pBK-RSV and PBK-CMV both of which are available from Stratagene, and pTRES which is available from Clontech.

A nucleic acid expression construct or construct system useful herein to up-regulate a factor may comprise transcriptional regulatory sequences in cis to endogenous sequences encoding Ang-1 or fibulin 5. By "in cis" is meant that the regulatory sequence is on the same DNA molecule as the sequence it is regulating. Alternatively, an expression construct or construct system useful to up-regulate a factor may comprise translational regulatory sequences in trans to endogenous sequences encoding Ang-1 or fibulin 5. By "in trans" is meant that the regulatory sequence is present on a different molecule of DNA than the sequence it is regulating.

Gene "knock-in" techniques well-known in the art can be used to introduce cis acting transcriptional regulatory sequences into the genome of the cell (U.S. Pat. Nos. 5,487,992, 5,464,764, 5,387,742, 5,360,735, 5,347,075, 5,298,422, 5,288,846, 5,221,778, 5,175,385, 5,175,384, 5,175,383 and 4,736,866, each of which is incorporated by reference, including any drawings, as if fully set forth herein. See also, International publications WO 94/23049, WO93/14200, WO 94/06908 and WO 94/28123. For additional general information on the technique, see Burke and Olson, Methods in Enzymology, 194:251 270, 1991; Capecchi, Science 244: 1288 1292, 1989; Davies et al., Nucleic Acids Research, 20 (11) 2693 2698, 1992; Dickinson et al., Human Molecular Genetics, 2(8):1299 1302, 1993; Duff and Lincoln, "Insertion of a pathogenic mutation into a yeast artificial chromosome containing the human APP gene and expression in ES cells", Research Advances in Alzheimer's Disease and Related Disorders, 1995; Huxley et al., Genomics, 9:742 750 1991; Jakobovits et al., Nature, 362:255 261 1993; Lamb et al., Nature Genetics, 5: 22 29, 1993; Pearson and Choi, Proc. Natl. Acad. Sci. USA, 1993, 90:10578 82; Rothstein, Methods in Enzymology, 194:281 301, 1991; Schedl et al., Nature, 362: 258 261, 1993 and Strauss et al., Science, 259:1904 1907, 1993.

The nucleic acid expression constructs of the present invention can be introduced into endothelial cells using any of a number of methods including, but not limited to, direct microinjection of DNA, protoplast fusion, diethylaminoethyldextran and calcium phosphate-mediated transfection, electroporation, lipofection, adenoviral transfection, retroviral transduction and others. Such methods are well-known in the art and any of them are within the scope of this invention.

The vector system is used to infect autologous or exogenous endothelial cells with the nucleic acid constructs that, in turn, express Ang-1 and fibulin 5. Preferably, the cells are genetically altered ex vivo, although in-vivo genetic alteration of xenogenic tissue followed by cell harvesting can also be used. If xenogenic cells are used, measures must be taken prior to or during administration to reduce the possibility of rejection. Numerous methods for accomplishing this are known to those skilled in the art.

All parts of the eye, including the cornea, sclera, trabeculum, iris, lens, vitreous humor, and retina can be treated by the present invention.

The Cornea: The cornea is the eye's outermost layer. It is the clear, dome-shaped surface that covers the front of the eye. The cornea is composed of five layers. The epithelium is a layer of cells that forms the surface. It is only about 5-6 cell layers thick and quickly regenerates when the cornea is injured. If an injury penetrates more deeply into the cornea, scarring may occur and leave opaque areas, causing the cornea to lose its clarity and luster. Immediately below the epithelium is Bowman's membrane, a protective layer that is very tough and difficult to penetrate. The stroma, the thickest layer of the cornea, lies just beneath Bowman's membrane and is composed of tiny collagen fibrils aligned in parallel, an arrangement that provides the cornea with its clarity. Descemet's membrane underlies the stroma and is just above the innermost corneal layer, the endothelium. The endothelium is just one cell layer in thickness, and serves to pump water from the cornea to the aqueous, keeping it clear. If damaged or diseased, these cells will not regenerate.

As the eye ages, the cornea can become more opaque. Opacification can take many forms. The most common form of opacification affects the periphery of the cornea, and is termed "arcus senilis," or "arcus." This type of opacification initially involves deposition of lipids into Descemet's membrane. Subsequently, lipids deposit into Bowman's membrane and possibly into the stroma as well. Arcus senilis is usually not visually significant, but is a cosmetically noticeable sign of aging. There are other age related corneal opacifications, however, which may have some visual consequences. These include central cloudy dystrophy of Francois, which affects the middle layers of the stroma, and posterior crocodile shagreen, which is central opacification of the posterior stroma. Opacification, by scattering light, results in progressive reduction of visual contrast and visual acuity.

Opacification of the cornea develops as a result of a number of factors, including, by way of example: degeneration of corneal structure; cross-linking of collagen and other proteins by metalloproteinases; ultraviolet (IV) light damage; oxidation damage; and buildup of substances like calcium salts, protein waste, and excess lipids.

There is no established treatment for slowing or reversing corneal changes other than surgical intervention. For example, opaque structures can be scraped away with a blunt instrument after first removing the epithelium, followed by smoothing and sculpting the corneal surface with a laser beam. In severe cases of corneal scarring and opacification, corneal transplantation has been the only effective approach.

Another common ocular disorder that adversely affects the cornea as well as other structures within the eye is keratoconjunctivitis sicca, commonly referred to as "dry eye syndrome" or "dry eye." Dry eye can result from a host of causes, and is frequently a problem for older people. The disorder is associated with a scratchy sensation, excessive secretion of mucus, a burning sensation, increased sensitivity to light, and pain. Dry eye is currently treated with "artificial tears," a commercially available product containing a lubricant such as low molecular weight polyethylene glycol. Surgical treatment, also, is not uncommon, and usually involves insertion of a punctal plug so that lacrimal secretions are retained in the eye. However, both types of treatment are problematic: surgical treatment is invasive and potentially risky, while artificial tear products provide only very temporary and often inadequate relief.

The Sclera: The sclera is the white of the eye. In younger individuals, the sclera has a bluish tinge, but as people grow older, the sclera yellows as a result of age-related changes in the conjunctiva. Over time, UV and dust exposure may result in changes in the conjunctival tissue, leading to pingecula and pterygium formation. These ocular growths can further cause breakdown of scleral and corneal tissue. Currently, surgery, including conjunctival transplantation, is the only accepted treatment for pingeculae and pterygia.

The Trabeculum: The trabeculum, also referred to as the trabecular meshwork, is a mesh-like structure located at the iris-sclera junction in the anterior chamber of the eye. The trabeculum serves to filter aqueous fluid and control its flow from the anterior chamber into the canal of Schlemm. As the eye ages, debris and protein-lipid waste may build up and clog the trabeculum, a problem that results in increased pressure within the eye, which in turn can lead to glaucoma and damage to the retina, optic nerve, and other structures of the eye. Glaucoma drugs can help reduce this pressure, and surgery can create an artificial opening to bypass the trabeculum and reestablish flow of liquid out of the vitreous and aqueous humor. There is, however, no known method for preventing a build-up of debris and protein-lipid waste within the trabeculum.

The Iris and Pupil: With age, dilation and constriction of the iris in response to changes in illumination become slower, and its range of motion decreases. Also, the pupil becomes progressively smaller with age, severely restricting the amount of light entering the eye, especially under low light conditions. The narrowing pupil and the stiffening, slower adaptation, and constriction of the iris over time are largely responsible for the difficulty the aged have in seeing at night and adapting to changes in illumination. The changes in iris shape, stiffness, and adaptability are generally thought to come from fibrosis and cross-linking between structural proteins. Deposits of protein and lipid wastes on the iris over time may also lighten its coloration. Both the light-colored deposits on the iris, and narrowing of the pupil, are very noticeable cosmetic markers of age that may have social implications for individuals. There is no standard treatment for any of these changes, or for changes in iris coloration with age.

The Lens: With age, the lens yellows, becomes harder, stiffer, and less pliable, and can opacity either diffusely or in specific locations. Thus, the lens passes less light, which reduces visual contrast and acuity. Yellowing also affects color perception. Stiffening of the lens as well as the inability of the muscle to accommodate the lens results in a condition generally known as presbyopia. Presbyopia, almost always occurring after middle age, is the inability of an eye to focus correctly. This age-related ocular pathology manifests itself in a loss of accommodative ability, i.e., the capacity of the eye, through the lens, to focus on near or far objects by changing the shape of the lens to become more spherical (or convex). Both myopic and hyperopic individuals are subject to presbyopia. The age-related loss of accommodative amplitude is progressive, and presbyopia is perhaps the most prevalent of all ocular afflictions, ultimately affecting virtually all individuals during the normal human life span.

These changes in the lens are thought to be due to degenerative changes in the structure of the lens, including glycated crosslinks between collagen fibers, buildup of protein complexes, ultraviolet light degradation of structures, oxidation damage, and deposits of waste proteins, lipids, and calcium salts. Elastic and viscous properties of the lens are dependent on properties of the fiber membranes and cytoskeleton crystallins. The lens fiber membranes are characterized by an extremely high cholesterol to phospholipid ratio. Any changes in these components affect the deformability of the lens membrane. The loss of lens deformability has also been attributed to increased binding of lens proteins to the cell membranes.

Compensatory options to alleviate presbyopia currently include bifocal reading glasses and/or contact lenses, monovision intraocular lenses (IOLs) and/or contact lenses, multifocal IOLs, monovision and anisometropic corneal refractive surgical procedures using radial keratotomy (RK), photorefractive keratomileusis (PRK), and laser-assisted in situ keratomileusis (LASIK). No universally accepted treatments or cures are currently available for presbyopia.

Opacity of the lens results in an abnormal condition generally known as cataract. Cataract is a progressive ocular disease, which subsequently leads to lower vision. Most of this ocular disease is age-related senile cataract. The incidence of cataract formation is thought to be 60-70% in persons in their sixties and nearly 100% in persons eighty years or older. However, at the present time, there is no agent that has been clearly proven to inhibit the development of cataracts. Therefore, the development of an effective therapeutic agent has been desired. Presently, the treatment of cataracts depends upon the correction of vision using eyeglasses, contact lenses, or surgical operations such as insertion of an intra-ocular lens into the capsula lentis after extra-capsular cataract extraction.

In cataract surgery, the incidence of secondary cataract after surgery has been a problem. Secondary cataract is equated with opacity present on the surface of the remaining posterior capsule following extracapsular cataract extraction. The mechanism of secondary cataract is mainly as follows. After excising lens epithelial cells (anterior capsule), secondary cataract results from migration and proliferation of residual lens epithelial cells, which are not completely removed at the time of extraction of the lens cortex, onto the posterior capsule leading to posterior capsule opacification. In cataract surgery, it is impossible to remove lens epithelial cells completely, and consequently it is difficult to always prevent secondary cataract. It is said that the incidence of the above posterior capsule opacification is 40-50% in eyes that do not receive an intracapsular posterior chamber lens implant and 7-20% in eyes which do receive an intracapsular lens implant. Additionally, eye infections categorized as endophthalmitis have also been observed after cataract surgeries.

The Vitreous Humor: Floaters are debris particles that interfere with clear vision by projecting shadows on the retina. There currently is no standard treatment for reducing or eliminating floaters.

The Retina: A number of changes can occur in the retina with age. Atherosclerotic buildup and leakage in the retinal arteries can lead to macular degeneration as well as reduction of peripheral vision. The rods and cones can become less sensitive over time as they replenish their pigments more slowly. Progressively, all these effects can reduce vision, ultimately leading to partial or complete blindness. Retinal diseases such as age-related macular degeneration have been hard to cure. Current retinal treatments include laser surgery to stop the leaking of blood vessels in the eye.

The ophthalmic formulations may be administered in any form suitable for ocular drug administration, e.g., as a solution or suspension for administration as eye drops or eye washes, ointment, gel, liposomal dispersion, colloidal microparticle suspension, or the like, or in an ocular insert, e.g., in an optionally biodegradable controlled release polymeric matrix. The ocular insert can be implanted in the conjunctiva, sclera, pars plana, anterior segment, or posterior segment of the eye. Implants provide for controlled release of the formulation to the ocular surface, typically sustained release over an extended time period. Additionally, in a preferred embodiment, the formulation is entirely composed of components that are naturally occurring and/or as GRAS ("Generally Regarded as Safe") by the U.S. Food and Drug Administration.

The pharmaceutically acceptable carrier of the formulations of the invention may comprise a wide variety of non-active ingredients which are useful for formulation purposes and which do not materially affect the novel and useful properties of the invention.

By a "pharmaceutically acceptable" or "ophthalmologically acceptable" component is meant a component that is not biologically or otherwise undesirable, i.e., the component may be incorporated into an ophthalmic formulation of the invention and administered topically to a patient's eye without causing any undesirable biological effects or interacting in a deleterious manner with any of the other components of the formulation composition in which it is contained. When the term "pharmaceutically acceptable" is used to refer to a component other than a pharmacologically active agent, it is implied that the component has met the required standards of toxicological and manufacturing testing or that it is included on the Inactive Ingredient Guide prepared by the U.S. Food and Drug Administration.

In carriers that are at least partially aqueous one may employ thickeners, isotonic agents, buffering agents, and preservatives, providing that any such excipients do not interact in an adverse manner with any of the formulation's other components. It should also be noted that preservatives are not necessarily required in light of the fact that the metal complexer itself may serve as a preservative, as for example EDTA which has been widely used as a preservative in ophthalmic formulations.

Suitable thickeners will be known to those of ordinary skill in the art of ophthalmic formulation, and include, by way of example, cellulosic polymers such as methylcellulose (MC), hydroxyethylcellulose (HEC), hydroxypropylcellulose (HPC), hydroxypropylmethylcellulose (HPMC), and sodium carboxymethylcellulose (NaCMC), and other swellable hydrophilic polymers such as polyvinyl alcohol (PVA), hyaluronic acid or a salt thereof (e.g., sodium hyaluronate), and crosslinked acrylic acid polymers commonly referred to as "carbomers" (and available from B.F. Goodrich as Carbopol®. polymers). The preferred amount of any thickener is such that a viscosity in the range of about 15 cps to 25 cps is provided, as a solution having a viscosity in the aforementioned range is generally considered optimal for both comfort and retention of the formulation in the eye. Any suitable isotonic agents and buffering agents commonly used in ophthalmic formulations may be used, providing that the osmotic pressure of the solution does not deviate from that of lachrymal fluid by more than 2-3% and that the pH of the formulation is maintained in the range of about 6.5 to about 8.0, preferably in the range of about 6.8 to about 7.8, and optimally at a pH of about 7.4. Preferred buffering agents include carbonates such as sodium and potassium bicarbonate.

The pharmaceutically acceptable ophthalmic carrier used with the formulations of the invention may be of a wide range of types known to those of skill in the art. For example, the formulations of the invention can be provided as an ophthalmic solution or suspension, in which case the carrier is at least partially aqueous. The formulations may also be ointments, in which case the pharmaceutically acceptable carrier comprises an ointment base. Preferred ointment bases herein have a melting or softening point close to body temperature, and any ointment bases commonly used in ophthalmic preparations may be advantageously employed. Common ointment bases include petrolatum and mixtures of petrolatum and mineral oil.

The formulations of the invention may also be prepared as a hydrogel, dispersion, or colloidal suspension. Hydrogels are formed by incorporation of a swellable, gel-forming polymer such as those set forth above as suitable thickening agents (i.e., MC, HEC, HPC, HPMC, NaCMC, PVA, or hyaluronic acid or a salt thereof, e.g., sodium hyaluronate), except that a formulation referred to in the art as a "hydrogel" typically has a higher viscosity than a formulation referred to as a "thickened" solution or suspension. In contrast to such preformed hydrogels, a formulation may also be prepared so as to form a hydrogel in situ following application to the eye. Such gels are liquid at room temperature but gel at higher temperatures (and thus are termed "thermoreversible" hydrogels), such as when placed in contact with body fluids. Biocompatible polymers that impart this property include acrylic acid polymers and copolymers, N-isopropylacrylamide derivatives, and ABA block copolymers of ethylene oxide and propylene oxide (conventionally referred to as "poloxamers" and available under the Pluronic®. tradename from BASF-Wyandotte). The formulations can also be prepared in the form of a dispersion or colloidal suspension. Preferred dispersions are liposomal, in which case the formulation is enclosed within "liposomes," microscopic vesicles composed of alternating aqueous compartments and lipid bilayers. Colloidal suspensions are generally formed from microparticles, i.e., from microspheres, nanospheres, microcapsules, or nanocapsules, wherein microspheres and nanospheres are generally monolithic particles of a polymer matrix in which the formulation is trapped, adsorbed, or otherwise contained, while with microcapsules and nanocapsules, the formulation is actually encapsulated. The upper limit for the size for these microparticles is about 5 µm to about 10 µm.

The formulations may also be incorporated into a sterile ocular insert that provides for controlled release of the formulation over an extended time period, generally in the range of about 12 hours to 60 days, and possibly up to 12 months or more, following implantation of the insert into the conjunctiva, sclera, or pars plana, or into the anterior segment or posterior segment of the eye. One type of ocular insert is an implant in the form of a monolithic polymer matrix that gradually releases the formulation to the eye through diffusion and/or matrix degradation. With such an insert, it is preferred that the polymer be completely soluble and/or biodegradable (i.e., physically or enzymatically eroded in the eye) so that removal of the insert is unnecessary. These types of inserts are well known in the art, and are typically composed of a water-swellable, gel-forming polymer such as collagen, polyvinyl alcohol, or a cellulosic polymer. Another type of insert that can be used to deliver the present formulation is a diffusional implant in which the formulation is contained in a central reservoir enclosed within a permeable polymer membrane that allows for gradual diffusion of the formulation out of the implant. Osmotic inserts may also be used, i.e., implants in which the formulation is released as a result of an increase in osmotic pressure within the implant following application to the eye and subsequent absorption of lachrymal fluid.

The invention also pertains to ocular inserts for the controlled release of combinations of the metal complexer and transport enhancer. These ocular inserts may be implanted into any region of the eye, including the sclera and the anterior and posterior segments. One such insert is composed of a controlled release implant containing a formulation that consists essentially of the active agent and a pharmaceutically acceptable carrier. The insert may be a gradually but completely soluble implant, such as may be made by incorporating swellable, hydrogel-forming polymers into an aqueous liquid formulation. The insert may also be insoluble, in which case the agent is released from an internal reservoir through an outer membrane via diffusion or osmosis.

The term "controlled release" refers to an agent-containing formulation or fraction thereof in which release of the agent is not immediate, i.e., with a "controlled release" formulation, administration does not result in immediate release of the agent into an absorption pool. The term is used interchangeably with "nonimmediate release" as defined in Remington: The Science and Practice of Pharmacy, Nineteenth Ed. (Easton, Pa.: Mack Publishing Company, 1995). In general, the term "controlled release" as used herein refers to "sustained release" rather than to "delayed release" formulations. The term "sustained release" (synonymous with "extended release") is used in its conventional sense to refer to a formulation that provides for gradual release of an agent over an extended period of time.

EXAMPLE 1

The following example describes the effect of Ang-1 on vascular permeability and retinal neovascularization in an in vivo model to treat an ophthalmic disorder such as retinopathy.

As described above, VEGF-A may be increased initially in preclinical DR as a mechanism to maintain the integrity of the retinal vascular bed. Vascular occlusion results in endothelial cell damage, a thickened basement membrane and changes in the red blood cell. In later stages, high VEGF-A production in ischemic areas, where VEGFR-2 is upregulated, then leads to loss of pericytes, vascular leakage and neovascularization. In proliferative DR (PDR), intra-ocular neovascularization is likely caused by high levels of VEGF-A in the vitreous derived from widespread production of this factor by ischemic retina.

Animal Models for diabetic retinopathy include hyperbaric oxygen models, diabetic Torri rat models, and animal models in which Bruch's membrane is intentionally breeched. Bruch's membrane separates the nourishing vascular layer called the choroid from the retina. A break in Bruch's membrane may allow the in-growth of vessels from the choroid to a position just beneath the retina. These vessels may then leak fluid or blood, initially distorting or blurring vision. Other models for retinopathy include transgenic mice expressing VEGF in photoreceptors/retinal pigment epithelium (RPE), repeated intraocular VEGF injection, sustained intravitreal release of VEGF, intraocular injection carrying VEGF, and intraocular dermal fibroblasts.

In this study, proliferative retinopathy was induced in white rabbits using autologous smooth muscle cells (SMC) expressing $VEGF_{165}$. As such, the present invention provides a method of inducing an ophthalmic disorder in a mammal. In one embodiment, the mammal is a non-human mammal. As described below, the results of this study indicate that administration of SMC expressing VEGF can serve as a model for retinopathy in non-diabetic mammals.

Autologous venous EC and SMC were isolated from the jugular veins of NZ white rabbits. EC harvesting was performed using incubation with collagenase 1 mg/ml for 15 min at 37° C. (Weisz A, Circulation, 2001). EC were identified based on their morphology of monolayer and cobblestone appearance under light inverted microscopy. Assurance of EC identification was done using immunohistochemical staining for the EC specific marker, vWF. Isolated EC were cultured in MI 99 supplemented with 20% fetal calf serum, penicillin 100 units/ml, streptomycin 0.1 mg/ml, amphotericin B 2.5 ug/ml, L-glutamate 2 mM, bFGF 2.5 ng/ml, and heparin 100 units/ml.

SMC were isolated by explant outgrowth from 2×2 mm pieces of vein segment incubated on fibronectin coated plates. SMC were identified based on their morphology of spindle shape and "hills & valley" appearance under light inverted microscopy. Assurance of SMC identification was done using immunohistochemical staining for the SMC specific marker αSMC Actin. Cells were cultured in Dulbecco's Modified Eagles Medium (DMEM) supplemented with 10% fetal calf serum, L glutamine 2 mM, penicillin 100 units/ml, streptomycin 0.1 mg/ml, amphotericin B 2.5 ug/ml, bFGF 2 ng/ml and heparin 100 units/ml.

After confirmation of both cell types, the cells were expanded and transduced with pseudo-typed retroviral vectors. SMC were transduced with $VEGF_{165}$-GFP encoding vector and EC were transduced with Ang-1 GFP encoding vector. Transduction of vascular cells was performed using retroviral vectors according to standard methods (Kahn M, Circ Res 1992). EC or SMC ($5 \times 10^5$ cells) at passage 3-6 after harvesting were seeded on 60 mm fibronectin-coated plates 24 hr prior to viral transduction. One hour prior to transduction, the medium was replaced with serum-free MI99 medium containing 0.1 mg/ml of the cationic polymer DEAE-dextran (Sigma, USA). Following pre-conditioning, the cells were washed three times with phosphate-buffered saline (PBS). Transduction was performed by incubation of the cells for 4 hours, with supernatants containing viruses collected and filtered (0.45 pm) freshly from the virus producing packaging cell lines. At the end of the incubation period the vector-containing medium was replaced with EC or SMC growth medium, respectively. Genetically modified cells were grown in G418 selection medium for 2-4 days until at least 90% of the expressed the transduced genes. Transduced cells were monitored for GFP and trans-gene expression. Ang-1 or $VEGF_{165}$ protein expression by the retrovirally transduced cells was confirmed by immunohistochemistry, ELISA, and Western blot analysis of the conditioned medium.

Identity and viability of the transduced cells was confirmed prior to administration. Then, $5 \times 10^6$ transduced EC and $5 \times 10^6$ transduced SMC were trypsinized, washed to remove serum and any growth-medium supplements, and mixed in 3 ml of saline. The cells were administered as described below by intravitreal injection.

The experimental groups for this study included: low dose SMC ($1.3 \times 10^6$ cells) expressing VEGF, high dose SMC ($2.5 \times 10^6$ cells) expressing VEGF, SMC expressing VEGF and EC expressing Ang-1 (both simultaneous and sequential administration), and SMC expressing Lac Z as a control.

For the SMC expressing VEGF group, a baseline electroretinographic (ERG) was obtained in each eye of all animals prior to intravitreal injection. ERGs were also obtained post-injection and at 5 or 8 weeks post-injection. Fluorescein angiography (FA) was performed at baseline and during weekly clinical exams post-injection for 5 to 8 weeks post-injection. Histology and Enzyme-Linked Immunosorbent Assay (ELISA) was performed on the eyes 5 or 8 weeks post-injection.

For the group with sequential injections of SMC expressing VEGF followed by EC expressing Ang-1 one week later, a baseline ERG was obtained in each eye of all animals prior to intravitreal injection of VEGF. ERGs were also obtained post-injection of VEGF, post-injection of Ang-1 and at 5 weeks post-injection of VEGF. FA was performed at baseline and during weekly clinical exams post injection for 5 weeks post-injection. Histology, ELISA and polymerase chain reaction (PCR) were performed on the eyes 5 weeks post-injection.

For the group with simultaneous injection of both SMC expressing VEGF and EC expressing Ang-1, a baseline ERG was obtained in each eye of all animals prior to intravitreal injection. ERGs were also obtained post-injection, and at 5 weeks post-injection. FA was performed at baseline and during weekly clinical exams post injection for 5 weeks post-injection. Histology, ELISA and PCR were performed on the eyes 5 weeks post-injection.

FIG. 1 shows the normal vasculature in the eye of a white rabbit. Specifically, fluorescein angiography (FA) was performed, in which fluorescein was injected intravenously, followed by an angiogram obtained by photographing the fluorescence emitted after illumination of the retina with blue light at a wavelength of 490 nanometers. There was no hemorrhaging or leakage of the blood vessels in the normal untreated eye.

Figure 2:
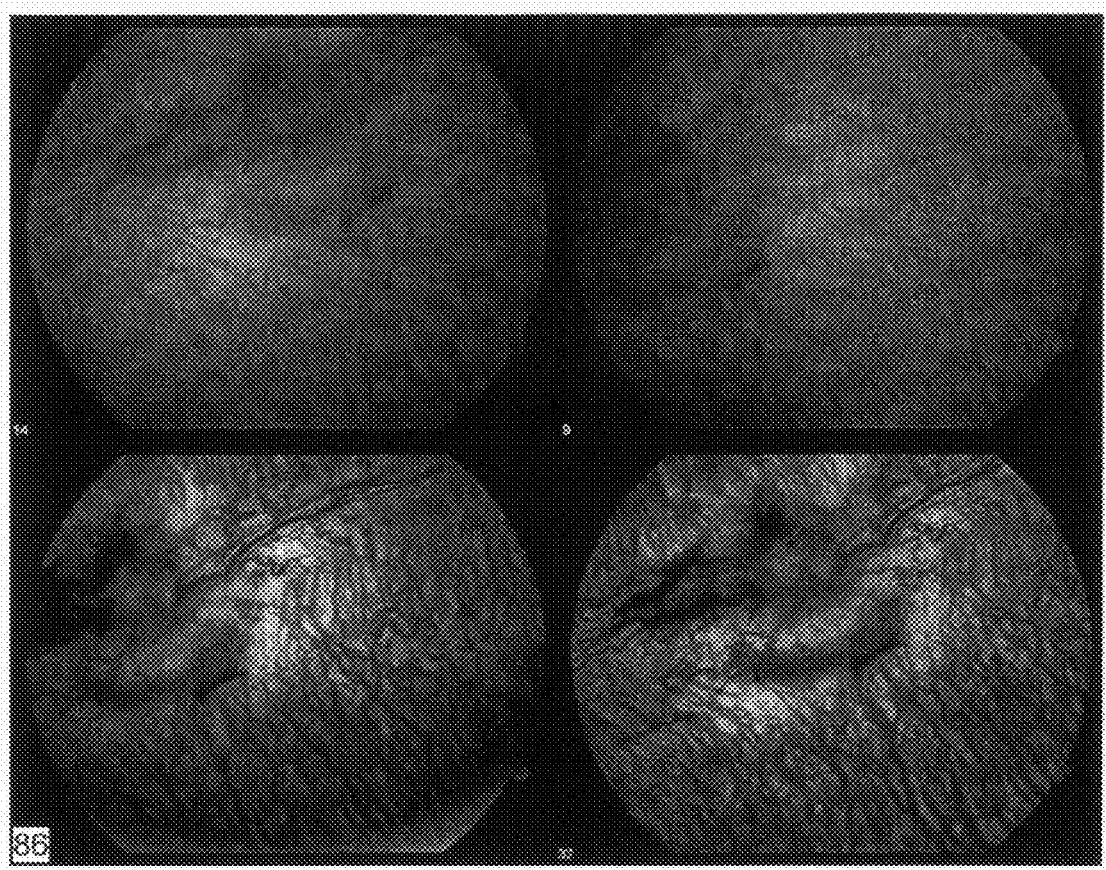
FIG. 2 is a panel of photographs illustrating the retinal blood vessel architecture in a rabbit eye 1 week post-injection of a high dose of SMC expressing VEGF.
Figure 3:
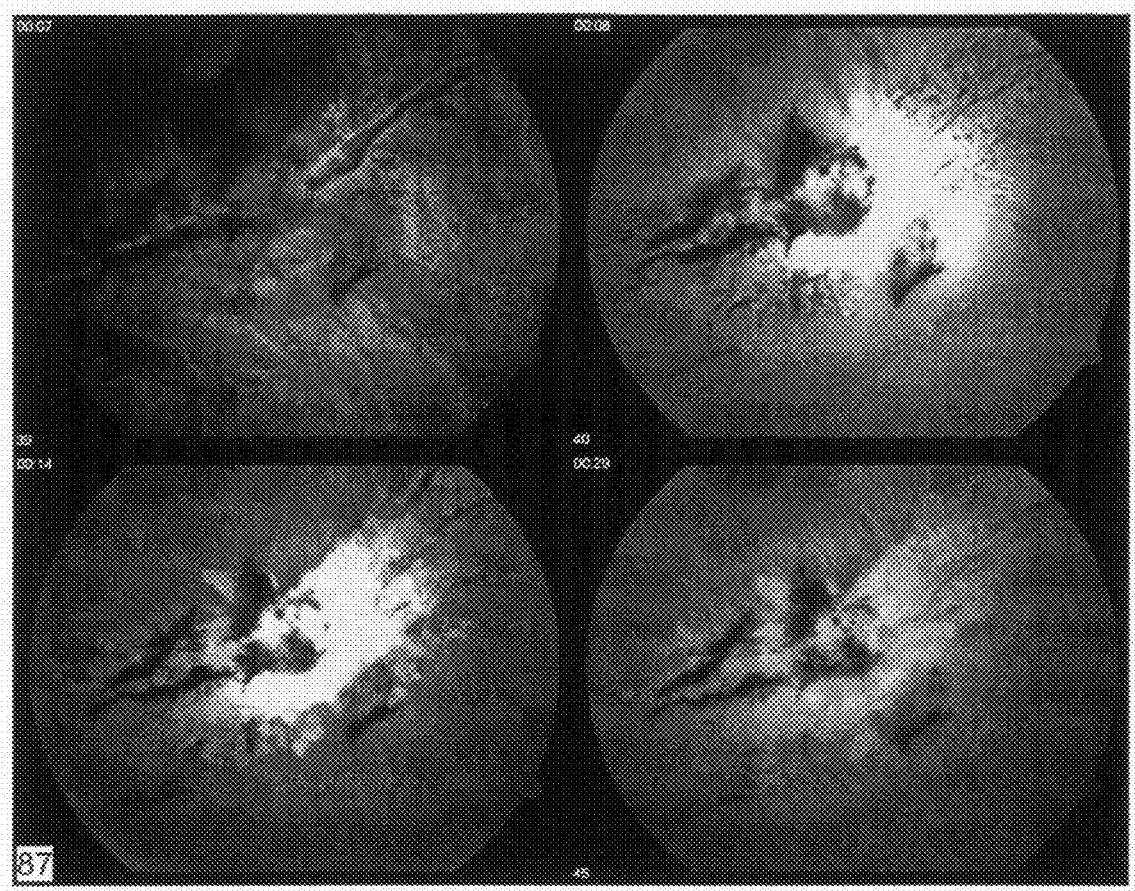
FIG. 3 is a series of photographs demonstrating the retinal blood vessel architecture in a rabbit eye 1 week post-injection of a high dose of SMC expressing VEGF.
Figure 4:
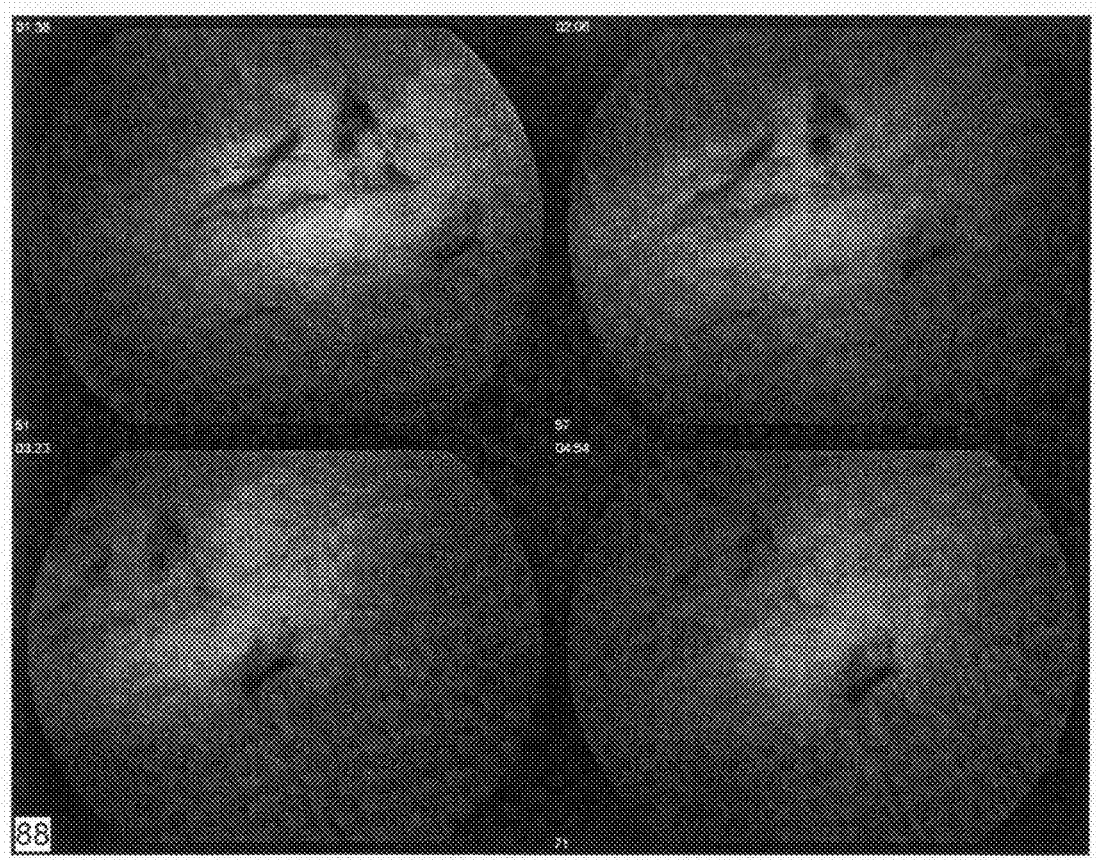
FIG. 4 is a series of photographs showing the retinal blood vessel architecture in a rabbit eye 1 week post-injection of a high dose of SMC expressing VEGF.
Figure 5:
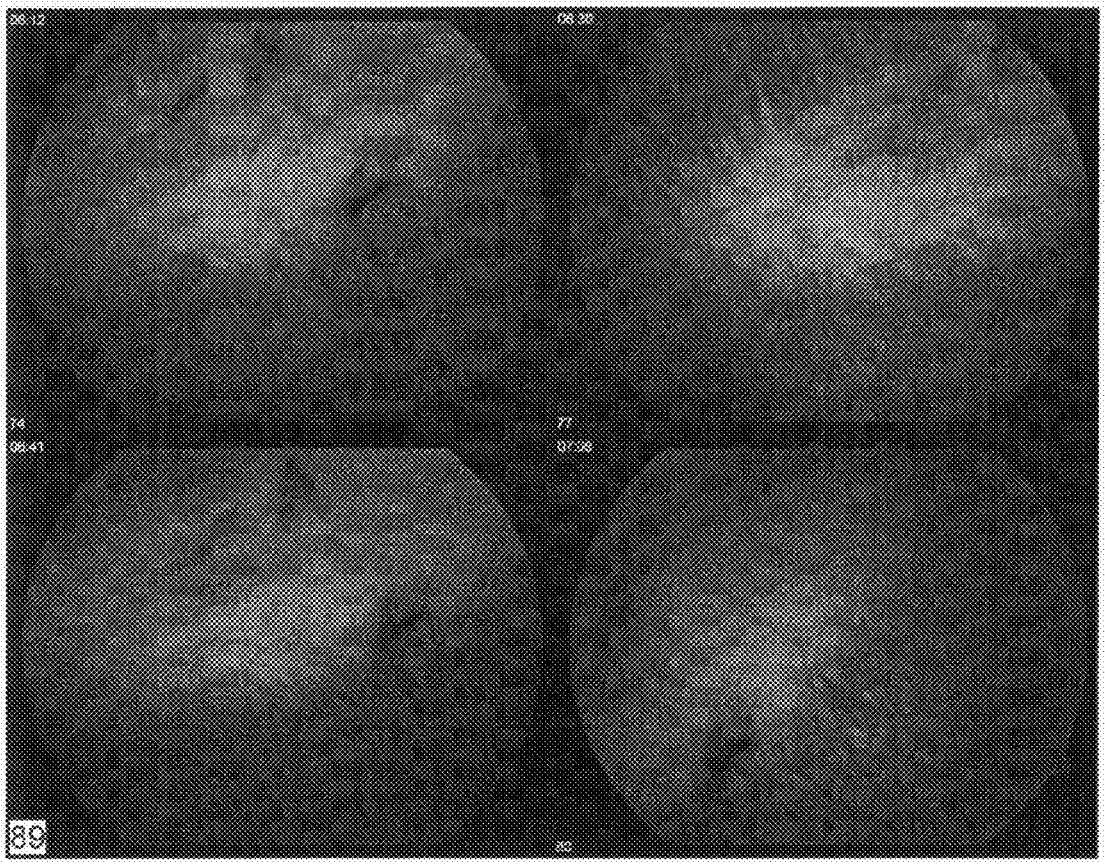
FIG. 5 is series of photographs showing the retinal blood vessel architecture in a rabbit eye 1 week post-injection of a high dose of SMC expressing VEGF.

In order to determine if the administration of VEGF could induce retinopathy, $2.5 \times 10^6$ SMC (high dose) expressing VEGF were injected intravitreally into white rabbits. By one week post-injection, the SMC expressing VEGF resulted in the formation of new retinal blood vessels, hemorrhage in front of the retina (preretinal hemorrhage), and intravitreal hemorrhage (FIG. 2). Time-lapse photography was performed with photographs taken at 7 minutes, 8 minutes, 14 minutes, 29 minutes, 1 hour and 38 minutes, 2 hours and 6 minutes, 3 hours and 23 minutes, 4 hours and 54 minutes, 6 hours and 12 minutes, 6 hours and 30 minutes, 6 hours and 41 minutes, and 7 hours and 6 minutes post-injection of fluorescein. As shown in FIGS. 3, 4, and 5, the SMC expressing VEGF also resulted in the development of leaky vessels, as indicated by the increased leakage of florescent dye from blood vessels over time. The blood-retinal barrier breaks down in neovascular lesions, which therefore fluoresce brightly and appear blurred as the dye leaks from the vascular lumina. The pre-existing preretinal and intravitreal hemorrhages can be seen in FIGS. 3-5 as dark masses.

Figure 6:
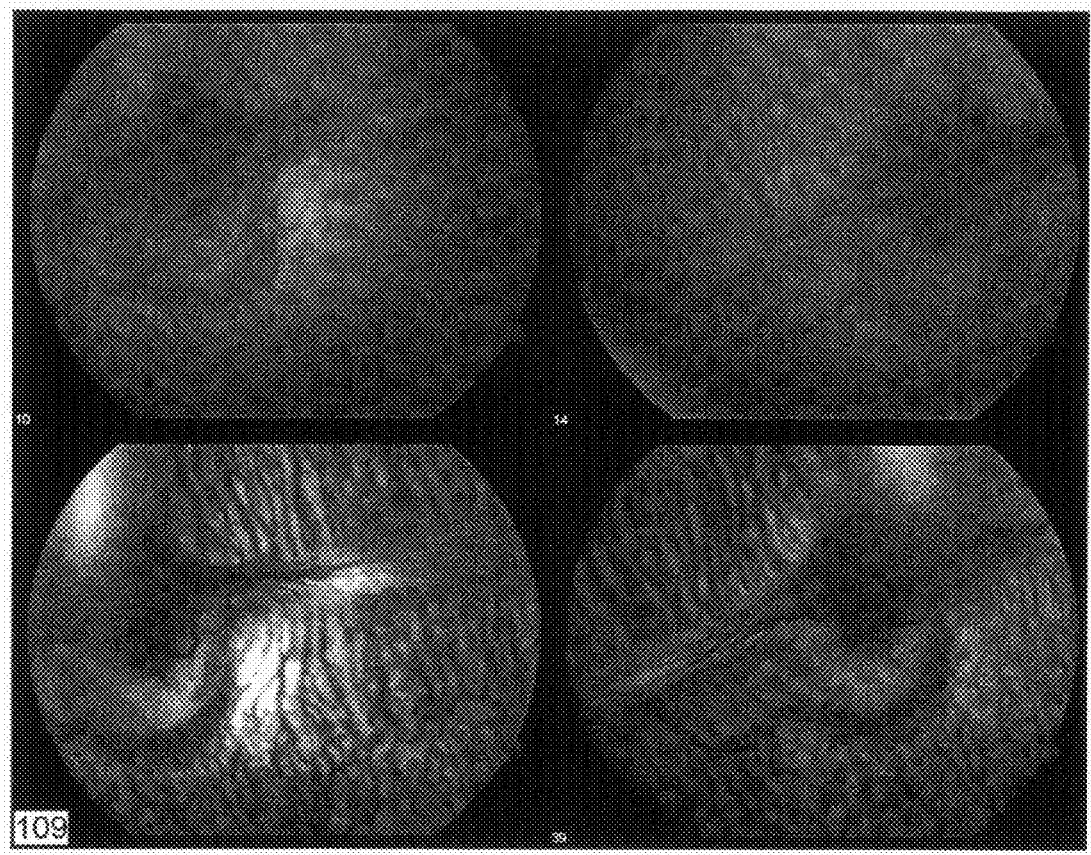
FIG. 6 is a series of photographs showing the retinal blood vessel architecture in a rabbit eye 3 weeks post-injection of a high dose of SMC expressing VEGF.
Figure 7:
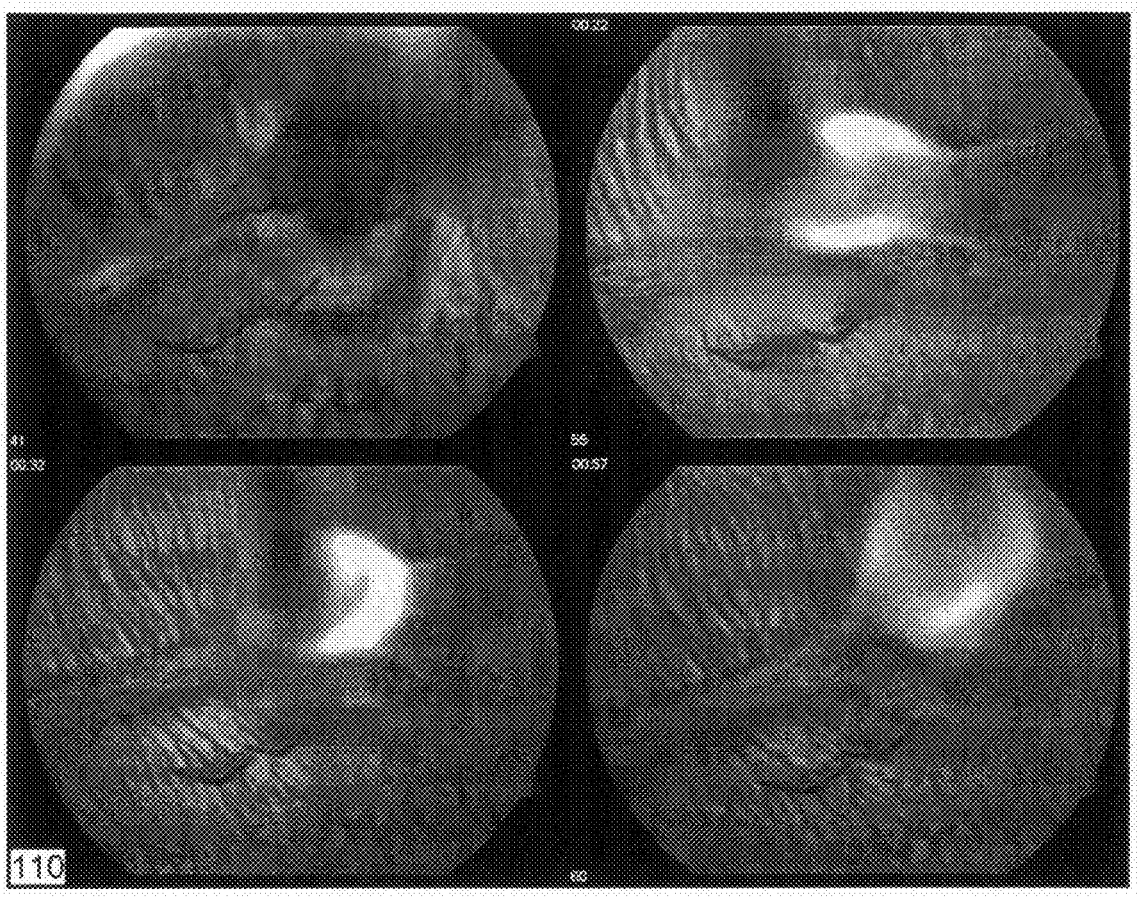
FIG. 7 is a series of photographs showing the retinal blood vessel architecture in a rabbit eye 3 weeks post-injection of a high dose of SMC expressing VEGF.
Figure 8:
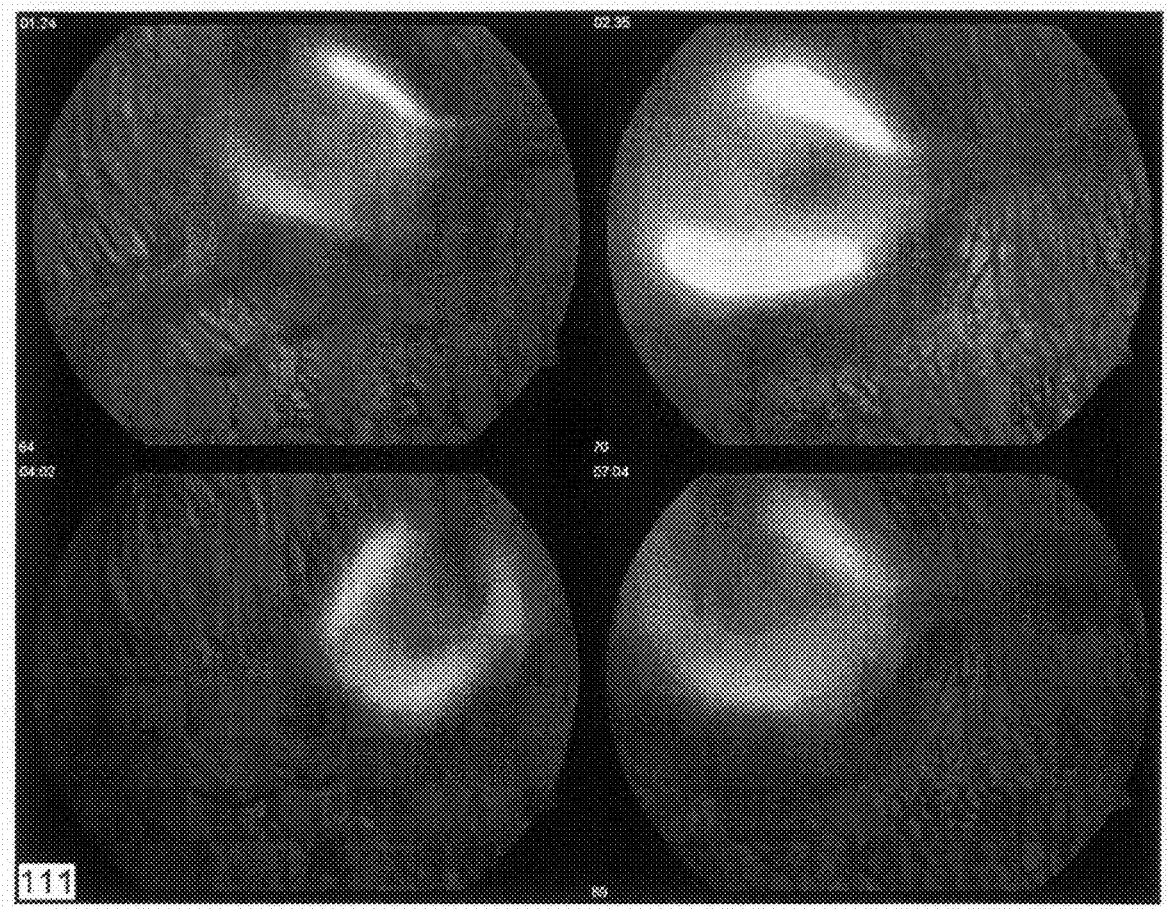
FIG. 8 is a panel of photographs showing the retinal blood vessel architecture in a rabbit eye 3 weeks post-injection of a high dose of SMC expressing VEGF.

FIG. 6 is a series of photographs demonstrating the optic disk neovascularization (NVD) typical of proliferative diabetic retinopathy (PDR) 3 weeks post-injection of SMC expressing VEGF. Moreover, time-lapse photography was performed with photographs taken at 22 minutes, 32 minutes, 57 minutes, 1 hour and 24 minutes, 2 hours and 35 minutes, 4 hours and 2 minutes, and 7 hours and 4 minutes post-injection of fluorescein. As shown in FIGS. 7 and 8, the SMC expressing VEGF also resulted in leaky vessels 3 weeks post-injection, as indicated by the increased leakage of florescent dye from blood vessels over time.

Figure 9:
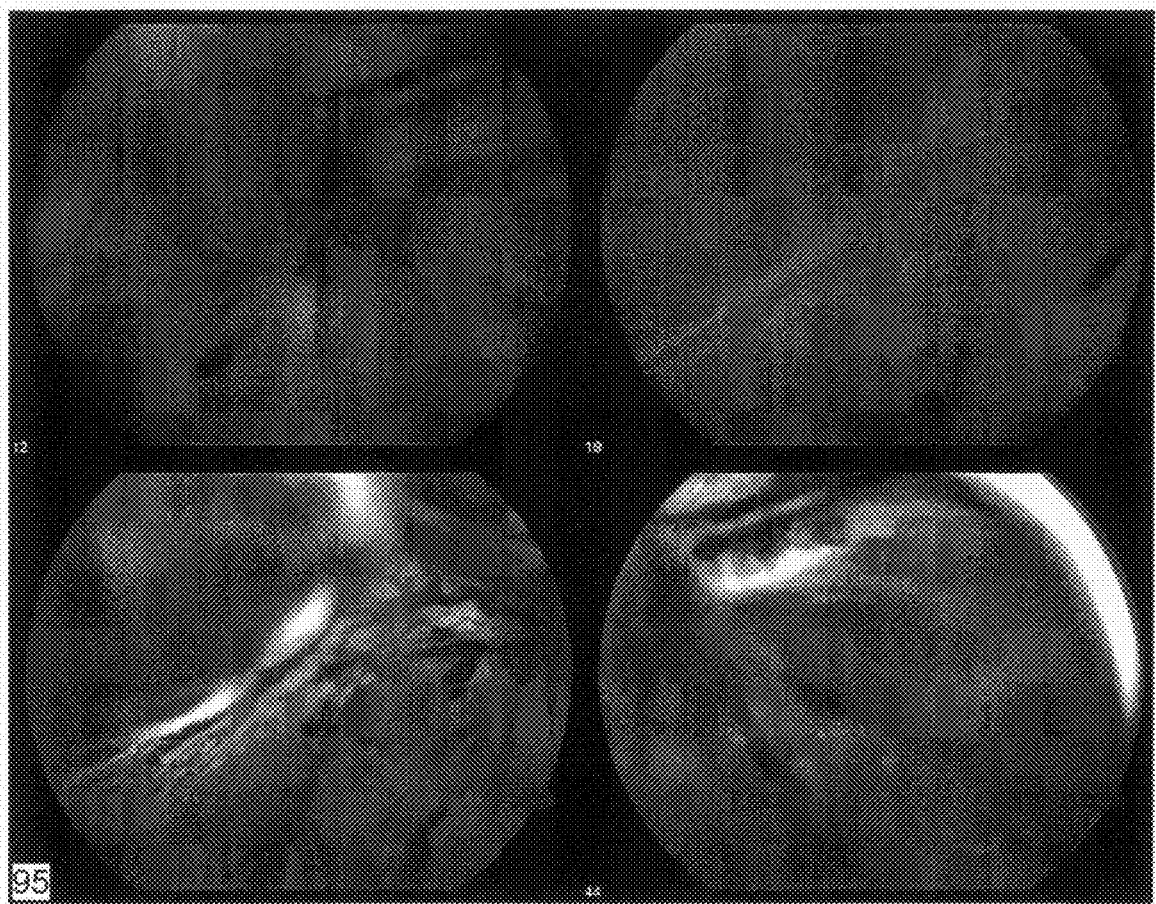
FIG. 9 is a series of photographs showing the retinal blood vessel architecture in a rabbit eye 4 weeks post-injection of a high dose of SMC expressing VEGF.
Figure 10:
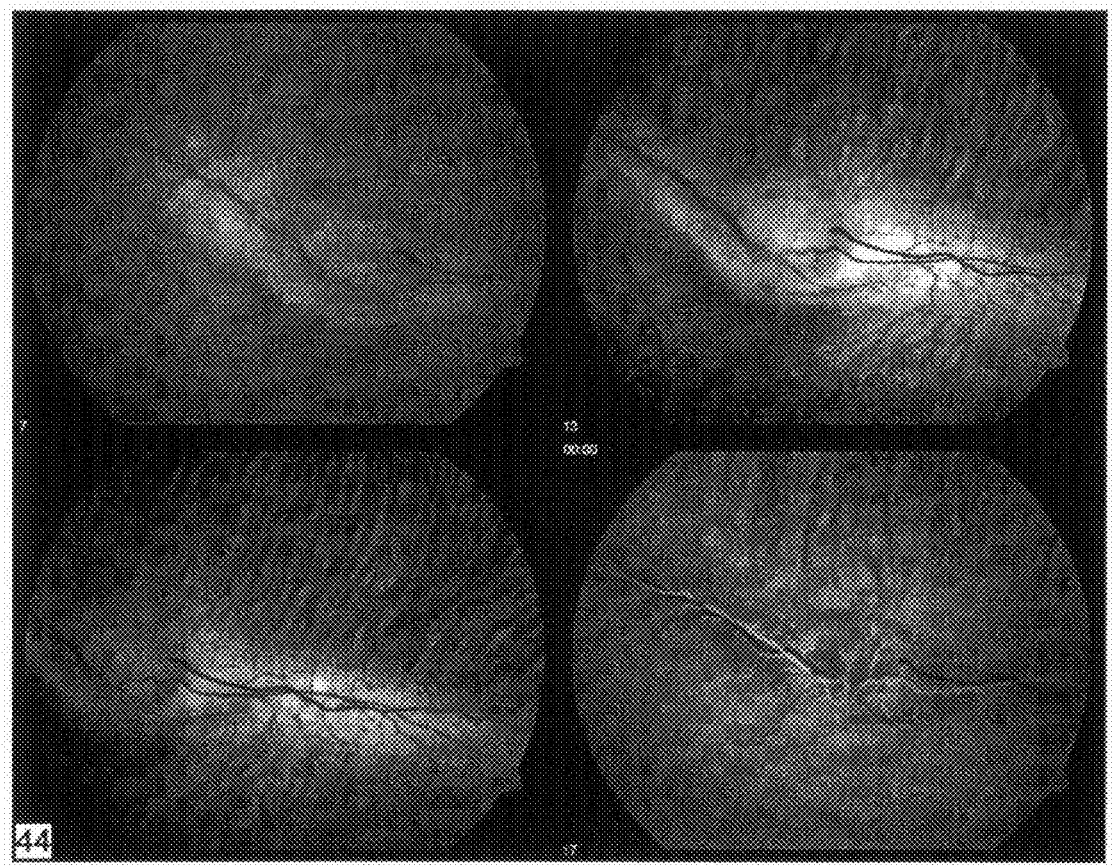
FIG. 10 is a panel of photographs demonstrating the retinal blood vessel architecture in a rabbit eye 4 weeks post-injection of SMC expressing Lac Z.

Four weeks post-injection of SMC expressing VEGF, massive hemorrhaging and blood vessel leakage was observed in the vitreous, which can lead to tractional retinal detachment (FIG. 9).

To confirm that the hemorrhaging and blood vessel leakage was due to VEGF expression, $2.5 \times 10^6$ SMC (high dose) expressing the Lac Z gene were injected intravitreally into white rabbits. No hemorrhaging or leaky blood vessels were seen 4 weeks post-injection of SMC expressing Lac Z, indicating that VEGF expression was critical for the induction of hemorrhaging and leaky blood vessels.

Proliferative vascular retinopathy resulted from intravitreal injection of autologous SMC expressing $VEGF_{165}$ as evidenced by vitreal and pre-retinal hemorrhages, new vessels leaking on late FA phases, vascular dilation and leakage, and tractional retinal detachment. The results presented above and shown in the Figures demonstrate that intravitreal injection of SMC expressing VEGF can serve as a model for diabetic retinopathy.

Figure 11:
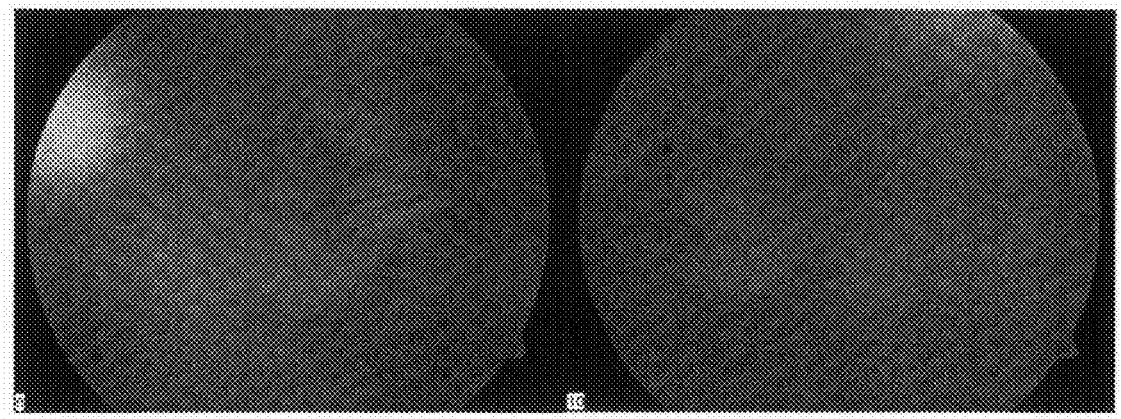
FIG. 11 is a series of photographs showing the retinal blood vessel architecture in a rabbit eye 5 weeks post-simultaneous injection of SMC expressing VEGF and EC expressing Ang-1.
Figure 12:
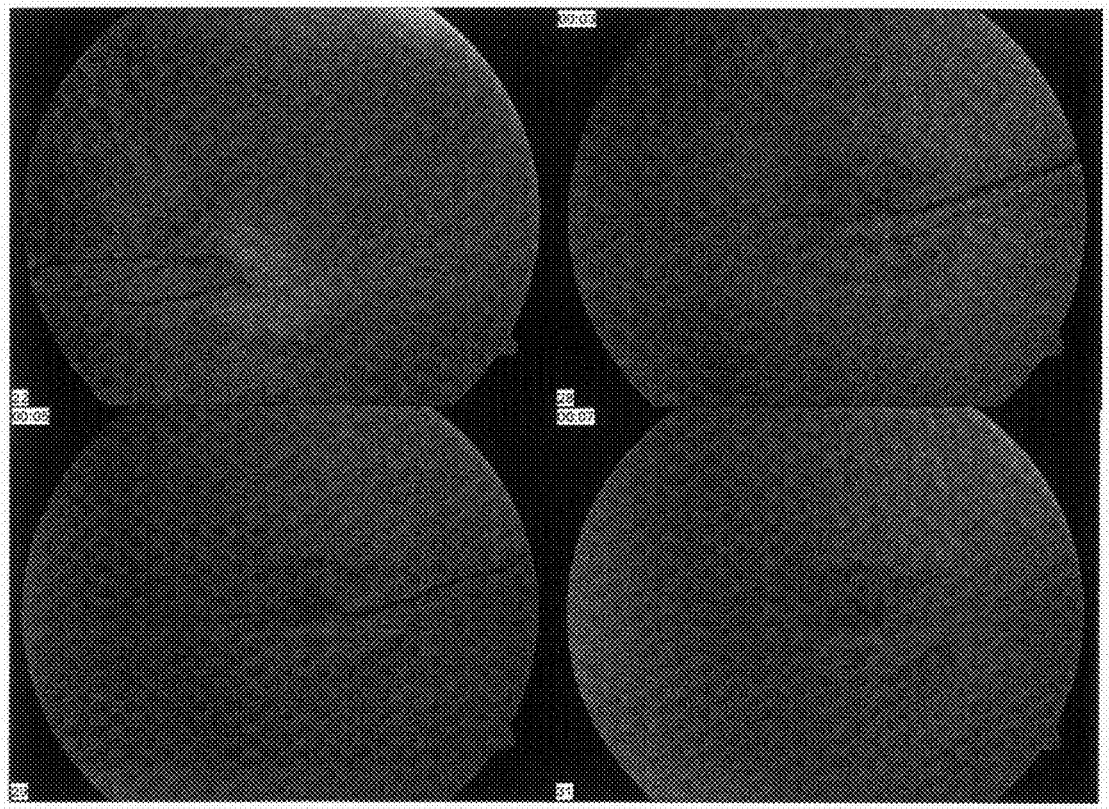
FIG. 12 is a series of photographs showing the retinal blood vessel architecture in a rabbit eye 5 weeks post-simultaneous injection of SMC expressing VEGF and EC expressing Ang-1.
Figure 13:
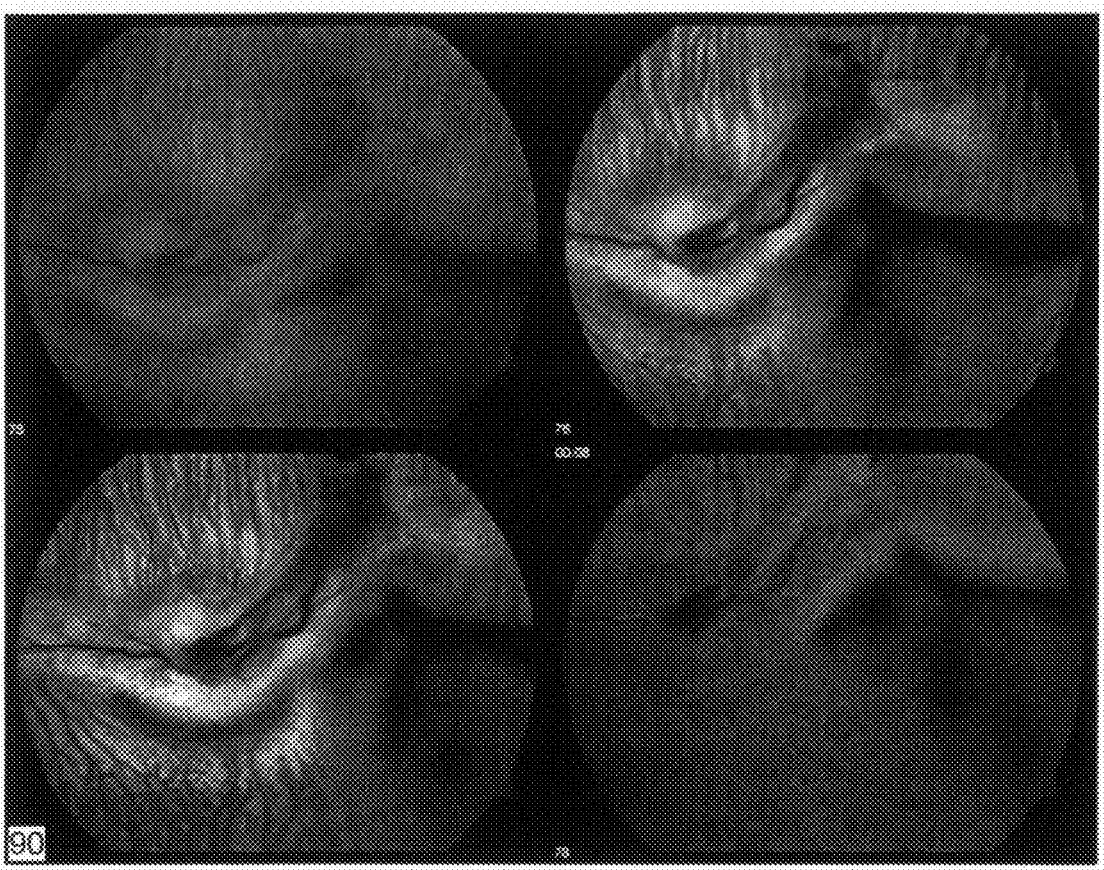
FIG. 13 is a series of photographs showing the retinal blood vessel architecture in a rabbit eye 4 weeks post-sequential injection of SMC expressing VEGF and EC expressing Ang-1.
Figure 14:
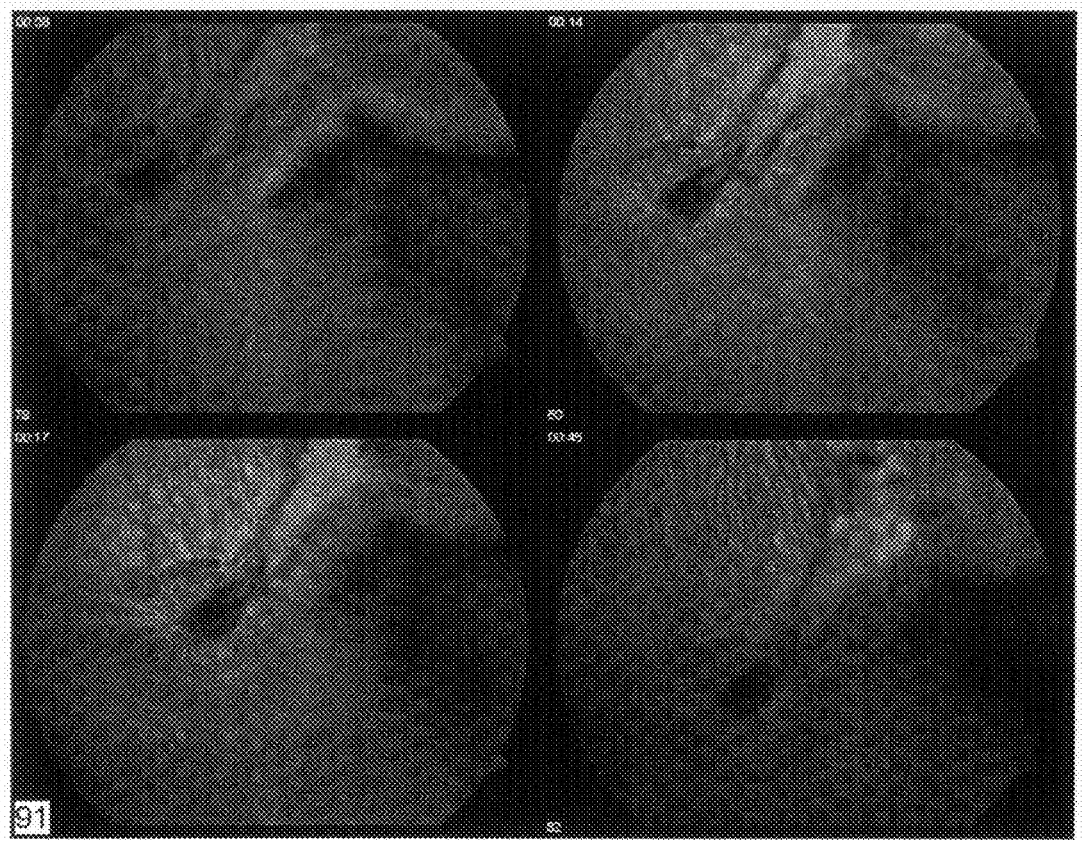
FIG. 14 is a series of photographs showing the retinal blood vessel architecture in a rabbit eye 4 weeks post-sequential injection of SMC expressing VEGF and EC expressing Ang-1.

To determine if EC expressing Ang-1 could reduce the hemorrhaging and blood vessel leakage induced by SMC expressing VEGF, simultaneous intravitreal injection of both SMC expressing VEGF and EC expressing Ang-1 was performed. As shown in FIG. 11, simultaneous injection of EC expressing Ang-1 and SMC expressing VEGF resulted in the preservation of the normal architecture in the retinal blood vessels 5 weeks post injection. Time-lapse photography was performed with photographs taken at 3 minutes, 5 minutes, and 7 minutes post-injection of fluorescein. As shown in FIG. 12, the co-administration of EC expressing Ang-1 prevented the development of hemorrhages and leaky vessels 5 weeks post-injection. The injection of EC expressing Ang-1 one week post-injection of SMC expressing VEGF also prevented the development of hemorrhages and leaky vessels (FIGS. 13-14).

Figure 15:
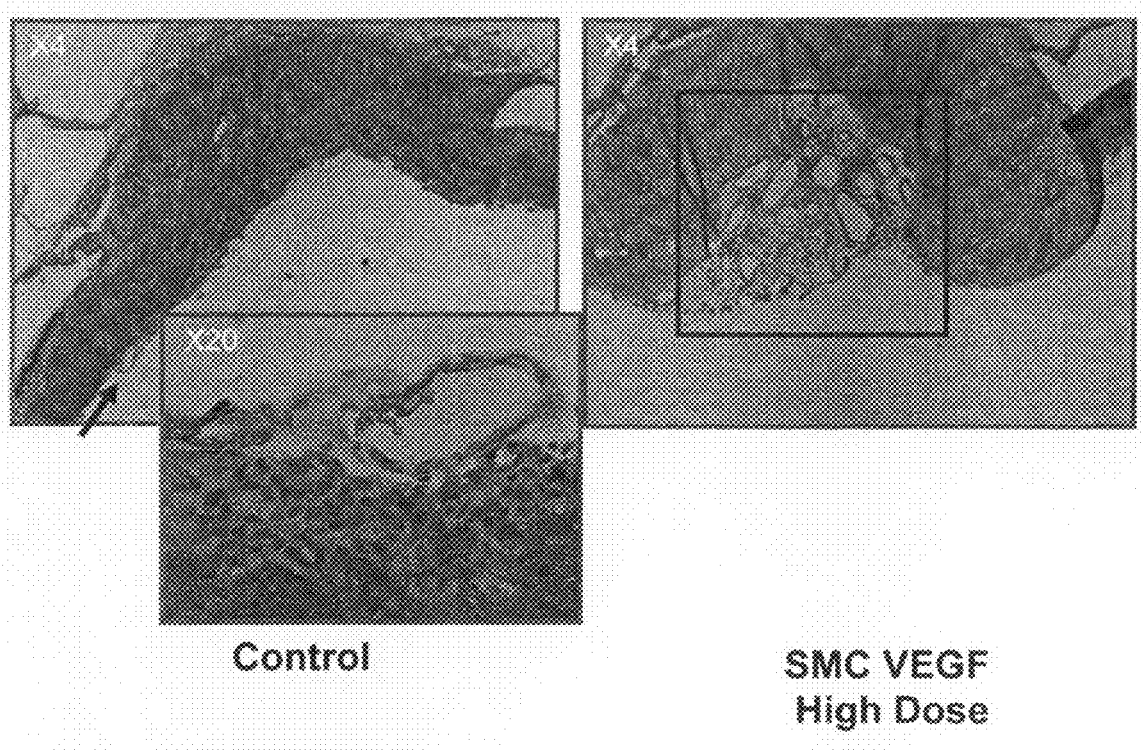
FIG. 15 is a panel of histology photographs depicting neovascularization in eyes that were administered the high dose of SMC expressing VEGF.
Figure 16:
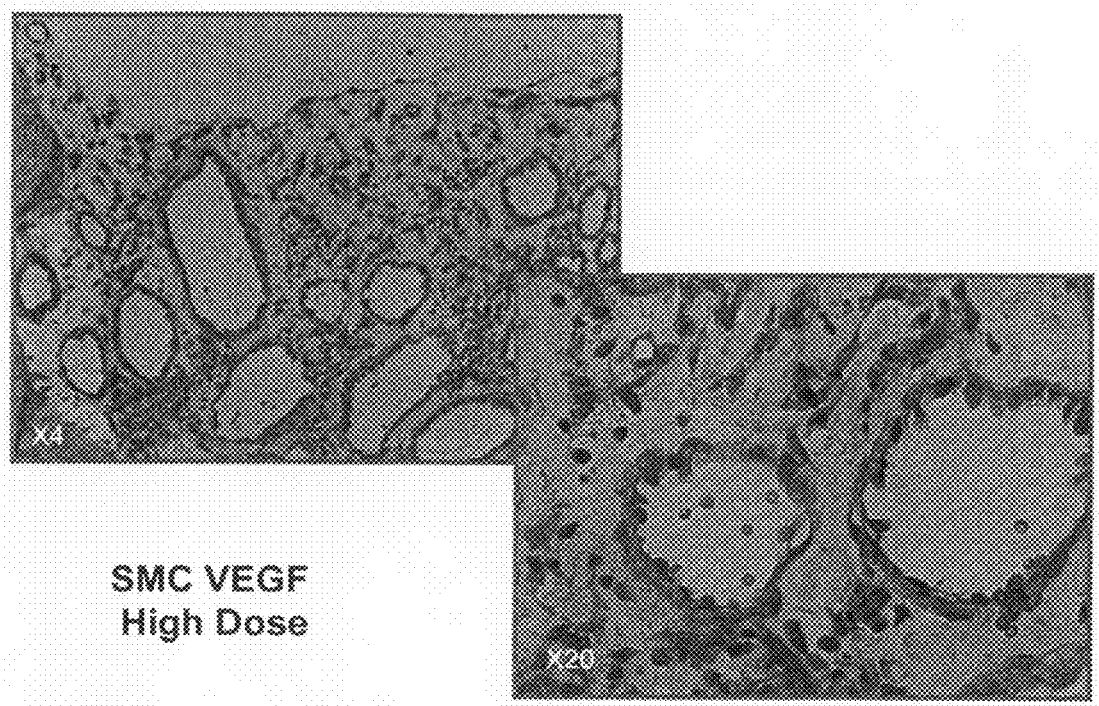
FIG. 16 is a panel of histology photographs showing neovascularization in eyes that were administered the high dose of SMC expressing VEGF.

Histological analysis confirmed that intravitreal injection of SMC expressing VEGF resulted in neovascularization of the optical disk (FIGS. 15 and 16).

A summary of the results is shown in Table 1. The severity of proliferative retinopathy was assessed by two independent scientists. The scores ranged from no response (least severe) to a 3+ (most severe). As shown in Table 1, both the high dose and low dose of SMC expressing VEGF resulted in a severe response, as indicated by leaky vessels and hemorrhaging. By contrast, the SMC expressing Lac Z resulted in no response in two animals and a 3+ response in one animal, which was likely due to the result of contamination. Both the simultaneous and subsequent injection of EC expressing Ang-1 prevented the response to SMC expressing VEGF, as indicated by reduced hemorrhaging and reduced leaky vessels.

As shown by the results described above, EC expressing Ang-1 reduced the vascular changes induced by autologous SMC cells expressing VEGF, indicating that EC expressing Ang-1 are useful in the treatment of diabetic retinopathy.

TABLE 1

Summary of results: Retinopathy

| Response | no | ± | 1+ | 2+ | 3+ |
|---|---|---|---|---|---|
| SMC VEGF-high dose |  |  |  | 1 | 2 |
| SMC Lac Z-high dose |  | 2 |  |  | 1 |
| SMC VEGF-low dose |  |  | 1 | 2 |  |
| SMC VEGF and after a week |  |  |  | 1 | 1 |
| EC Ang-1 high dose |  |  |  |  |  |
| SMC VEGF + EC Ang-1 |  |  |  | 1 | 1 |
| Simultaneous-high dose |  |  |  |  |  |

As a control, the amount of VEGF in untreated eyes and eyes treated with SMC expressing Lac Z was determined via ELISA (Table 2).

TABLE 2

Control SMC Lac Z

| | VEGF ELISA (pg/ml) | |
|---|---|---|
| Rabbit | Untreated Eye | Treated Eye |
| 7123 | 11.95 | 10.18 |
| HJK34 | 28.18 | 11.95 |
| 6824 | 17.64 | 29.17 |

The amount of VEGF and Ang-1 was determined in the eyes that were subject to the simultaneous injection of SMC expressing VEGF and EC expressing Ang-1. As shown in Table 3, the treated eyes had a greater amount of VEGF and Ang-1 as compared to the untreated eyes several weeks after injection.

TABLE 3

Simultaneous Injection VEGF + Ang-1 ELISA

| | VEGF ELISA (pg/ml) | | Ang-1 ELISA (pg/ml) | |
|---|---|---|---|---|
| Rabbit | Untreated Eye | Treated Eye | Untreated Eye | Treated Eye |
| 7235 | 0.70 | 1245.20 | 40.7 | 128.1 |
| 6781 | 0.00 | 1495.90 | 92.60 | 348.1 |

EXAMPLE 2

Experiments were performed to determine if angiogenic and/or cell proliferation genes were up or down-regulated in EC expressing Ang-1 as compared to naïve EC, and SMC expressing VEGF as compared to naïve SMC. The effect of conditioned medium from SMC expressing VEGF on both naïve and transduced EC was also determined.

Template cDNAs prepared from total RNA of human endothelial and smooth muscle cells were characterized using the Human Angiogenesis PathwayFinder™ PCR Array (SuperArray) with the RT2 SYBR Green/Fluorescein PCR master mix on the ABI 7000 cycler.

Table 3 shows the result of the analysis of 84 genes as described above. Less than a 2 fold change in expression was not considered to be significant. As shown in Table 3, a variety of angiogenic and cell proliferation genes are up or down-regulated.

| | | Fold change | | | |
|---|---|---|---|---|---|
| Symbol | Gene | EC Naive/EC Ang | SMC Naive/SMC VEGF | EC Naive/EC Naive incubated with SMC VEGF CM | EC Ang/EC Ang incubated with SMC VEGF CM |
| AKT/PKB | V-akt murine thymoma viral oncogene homolog 1 | 1.45 | −2.33 | 2.62 | 1.33 |
| ANGPT1 | Angiopoietin 1 | −1.01 | −2.37 | 1.41 | −2.55 |
| ANGPT2 | Angiopoietin 2 | −1.26 | 29.19 | 7.62 | 4.45 |
| ANGPTL3 | Angiopoietin-like 3 | −4.58 | 3.45 | −3.89 | −1.02 |
| ANGPTL4 | Angiopoietin-like 4 | −1.51 | −2.05 | −2.45 | −1.74 |
| ANPEP | Alanyl (membrane) aminopeptidase (aminopeptidase N, aminopeptidase M, microsomal aminopeptidase, CD13, p150) | 1.10 | −4.56 | 1.56 | −1.96 |
| BAI1 | Brain-specific angiogenesis inhibitor 1 | −2.77 | −1.41 | −4.89 | −1.72 |
| CCL11 | Chemokine (C-C motif) ligand 11 | −2.09 | −1.52 | 1.08 | 2.84 |
| CCL2 | Chemokine (C-C motif) ligand 2 | −2.80 | −7.35 | 1.50 | 2.50 |
| CDH5 | Cadherin 5, type 2, VE-cadherin (vascular epithelium) | −1.26 | −8.98 | −1.17 | −1.42 |
| COL18A1 | Collagen, type XVIII, alpha 1 | −1.92 | −2.97 | 1.03 | 1.21 |
| COL4A3 | Collagen, type IV, alpha 3 | −2.66 | −22.16 | −2.02 | 1.71 |
| CXCL1 | Chemokine (C—X—C motif) ligand 1 (melanoma growth stimulating activity, alpha) | −4.27 | −12.39 | −4.19 | −1.57 |
| CXCL10 | Chemokine (C—X—C motif) ligand 10 | −4.57 | −2.85 | −6.48 | −2.65 |
| CXCL3 | Chemokine (C—X—C motif) ligand 3 | −2.47 | 141.25 | −1.72 | −1.26 |
| CXCL5 | Chemokine (C—X—C motif) ligand 5 | −1.09 | −2.84 | 1.74 | −1.71 |
| CXCL6 | Chemokine (C—X—C motif) ligand 6 (granulocyte chemotactic protein 2) | −2.42 | −13.66 | −4.43 | −3.19 |
| CXCL9 | Chemokine (C—X—C motif) ligand 9 | −3.77 | 1.00 | −2.87 | −1.17 |
| ECGF1 | Endothelial cell growth factor 1 (platelet-derived) | −3.89 | −3.18 | −1.64 | 2.15 |

| Symbol | Gene | Fold change | | | |
|---|---|---|---|---|---|
| | | EC Naive/EC Ang | SMC Naive/SMC VEGF | EC Naive/EC Naive incubated with SMC VEGF CM | EC Ang/EC Ang incubated with SMC VEGF CM |
| EDG1 | Endothelial differentiation, sphingolipid G-protein-coupled receptor, 1 | 1.19 | −6.05 | 1.43 | −1.54 |
| EFNA1 | Ephrin-A1 | −1.42 | −6.23 | −1.02 | 1.10 |
| EFNA3 | Ephrin-A3 | −2.38 | −1271.77 | −2.29 | −1.31 |
| EFNB2 | Ephrin-B2 | −2.06 | −2.02 | −2.03 | 1.08 |
| EGF | Epidermal growth factor (beta-urogastrone) | 1.18 | −5.07 | 1.16 | −1.10 |
| ENG | Endoglin | 1.53 | −3.78 | 1.35 | −1.74 |
| EPHB4 | EPH receptor B4 | −2.22 | −3.36 | −2.53 | −1.51 |
| EREG | Epiregulin | −3.39 | 355.22 | 1.25 | 1.57 |
| FGF1 | Fibroblast growth factor 1 (acidic) | −2.08 | −3.61 | 1.40 | −2.63 |
| FGF2 | Fibroblast growth factor 2 (basic) | 17.91 | 1664.51 | 11.15 | −1.90 |
| FGFR3 | Fibroblast growth factor receptor 3 (achondroplasia, thanatophoric dwarfism) | −125433.22 | −6.61 | −106704.39 | 1.08 |
| FIGF | C-fos induced growth factor (vascular endothelial growth factor D) | −14.50 | −4.07 | −13.52 | −1.04 |
| FLT1 | Fms-related tyrosine kinase 1 (vascular endothelial growth factor/vascular permeability factor receptor) | 552.35 | −8.65 | 491.26 | −1.86 |
| HAND2 | Heart and neural crest derivatives expressed 2 | −10.87 | −4.33 | 1.03 | 4.43 |
| HGF | Hepatocyte growth factor (hepapoietin A; scatter factor) | −1.24 | −17.42 | 6.25 | 5.27 |
| HIF1A | Hypoxia-inducible factor 1, alpha subunit (basic helix-loop-helix transcription factor) | −2.33 | −3.60 | −1.10 | 1.45 |
| HPSE | Heparanase | −1.97 | −9.41 | −1.48 | −1.01 |
| ID1 | Inhibitor of DNA binding 1 | −3.30 | −8.36 | −5.32 | −1.70 |
| ID3 | Inhibitor of DNA binding 3, dominant negative helix-loop-helix protein | 11.06 | 1.26 | 11.93 | −1.05 |
| IFNA1 | Interferon, alpha 1 | −1.84 | −3.88 | −1.34 | 1.81 |
| IFNB1 | Interferon, beta 1, fibroblast | 1.02 | −8.43 | −2.20 | −1.99 |
| IFNG | Interferon, gamma | −2.66 | −3.36 | −2.02 | −1.17 |
| IGF1 | Insulin-like growth factor 1 (somatomedin C) | −2.12 | −2.98 | −9.51 | 1.18 |
| IL1B | Interleukin 1, beta | 11.08 | −9.17 | 56.30 | −1.18 |
| IL6 | Interleukin 6 (interferon, beta 2) | −2.73 | −4.74 | −1.84 | 1.11 |
| IL8 | Interleukin 8 | −3.14 | −10.15 | −1.50 | −1.01 |
| ITGAV | Integrin, alpha V (vitronectin receptor, alpha polypeptide, antigen CD51) | −5.11 | −3.74 | −3.06 | 1.12 |
| ITGB3 | Integrin, beta 3 (platelet glycoprotein IIIa, antigen CD61) | −1.44 | −2.79 | −2.16 | −1.92 |
| JAG1 | Jagged 1 (Alagille syndrome) | −2.72 | −3.68 | −1.28 | −1.08 |
| KDR | Kinase insert domain receptor (a type III receptor tyr kinase) | −2.02 | 2.15 | −1.00 | −1.12 |
| LAMA5 | Laminin, alpha 5 | −2.25 | −6.43 | −1.58 | 1.22 |
| LECT1 | Leukocyte cell derived chemotaxin 1 | −2.10 | −5.60 | −1.93 | 1.74 |
| LEP | Leptin (obesity homolog) | −1.26 | −3.98 | −2.02 | −1.31 |
| MDK | Midkine (neurite growth-promoting factor 2) | −1.81 | −3.13 | −2.47 | −2.37 |
| MMP2 | Matrix metallopeptidase 2 (gelatinase A, 72 kDa gelatinase, 72 kDa type IV collagenase) | 148.66 | −3.00 | 117.80 | −2.17 |
| MMP9 | Matrix metallopeptidase 9 (gelatinase B, 92 kDa gelatinase, 92 kDa type IV collagenase) | −1.06 | −1.09 | 2.86 | 1.77 |
| NOTCH4 | Notch homolog 4 (*Drosophila*) | 1.21 | −1.02 | 3.17 | −1.12 |
| NRP1 | Neuropilin 1 | −1.32 | −2.99 | 1.65 | 1.34 |
| NRP2 | Neuropilin 2 | −1.37 | −3.07 | 1.18 | 1.01 |
| PDGFA | Platelet-derived growth factor alpha polypeptide | −2.67 | −4.11 | −1.35 | 1.47 |

-continued

| Symbol | Gene | Fold change | | | |
|---|---|---|---|---|---|
| | | EC Naive/EC Ang | SMC Naive/SMC VEGF | EC Naive/EC Naive incubated with SMC VEGF CM | EC Ang/EC Ang incubated with SMC VEGF CM |
| PECAM1 | Platelet/endothelial cell adhesion molecule (CD31 antigen) | −1.77 | −5.31 | −1.02 | 1.20 |
| PF4 | Platelet factor 4 (chemokine (C—X—C motif) ligand 4) | −2.88 | −2.71 | −2.46 | −1.11 |
| PGF | Placental growth factor, vascular endothelial growth factor-related protein | 231.34 | 33.41 | 1100.73 | 2.26 |

What is claimed is:

1. A method of treating an ophthalmic condition or disorder comprising administering to a subject in need thereof a therapeutically effective amount of autologous endothelial cells comprising a nucleic acid construct comprising a polynucleotide sequence encoding Ang-1 operably linked to a promoter such that said endothelial cells express or over-express said Ang-1.

2. The method of claim 1, wherein said endothelial cells are administered by intra-vitreal injection.

3. The method of claim 1, wherein said ophthalmic disorder is selected from the group consisting of diabetic retinopathy and age-related macular degeneration (AMD).

4. The method of claim 3, wherein said Ang-1 induces angiogenesis, enhances endothelial cell survival, or prevents vascular leakage.

* * * * *